(12) United States Patent
Ray

(10) Patent No.: US 7,618,985 B2
(45) Date of Patent: Nov. 17, 2009

(54) ISOQUINOLINE DERIVATIVES

(75) Inventor: Peter Christopher Ray, Newhouse (GB)

(73) Assignee: N.V. Organon, Oss (NL)

( * ) Notice: Subject to any disclaimer, the term of this patent is extended or adjusted under 35 U.S.C. 154(b) by 0 days.

(21) Appl. No.: 11/633,973

(22) Filed: Dec. 5, 2006

(65) Prior Publication Data
US 2007/0135479 A1 Jun. 14, 2007

Related U.S. Application Data

(60) Provisional application No. 60/748,664, filed on Dec. 8, 2005.

(30) Foreign Application Priority Data

Dec. 8, 2005 (EP) ................................. 05111813

(51) Int. Cl.
*C07D 401/02* (2006.01)
*A61K 31/47* (2006.01)
(52) U.S. Cl. ........................ 514/309; 514/310; 546/141; 546/143
(58) Field of Classification Search ................. 546/141, 546/143; 514/309, 310
See application file for complete search history.

(56) References Cited

U.S. PATENT DOCUMENTS

2007/0135479 A1* 6/2007 Ray ........................... 514/309

FOREIGN PATENT DOCUMENTS

| EP | 1 403 255 A1 | 3/2004 |
|---|---|---|
| EP | 1 541 559 A1 | 6/2005 |
| EP | 1 550 660 A1 | 7/2005 |
| WO | WO 04/000955 | 12/2003 |
| WO | WO 2004/024717 | 3/2004 |
| WO | WO 2006/051290 | 5/2006 |

OTHER PUBLICATIONS

Chen, P. et al., "Identification of Novel and Potent Isoquinoline Aminooxazole-Based IMPDH Inhibitors," *Bioorg. Med. Chem. Lett.* 13, 2003, 1345-1348.
Elliott, R.L., et al., "2-(Aryloxymethyl) Azacyclic Analogues as Novel Nicotinic Acetylcholine Receptor (nAChR) Ligands," *Biorg. Med. Chem. Lett.*, 6, 1996, 2283-2288.
Hendrickson, J.B., et al., An Efficient Synthesis of Substituted Isoquinolines, *J. Org. Chem.* 48, 1983, 3344-3346.
Hirooka, Y., et al., "Therapeutic Potential of Rho-Kinase Inhibitors in Cardiovascular Diseases," *Am. J. Cardiovasc. Drugs*, 5(1), 2005, 31-39.
Hu, E. et al., "Rho Kinase as Potential Therapeutic Target for Cardiovascular Diseases . . . ," *Expert Opinion Ther. Targets*, 9(4), 2005, 715-736.
Kende, A.S. et al., "A Regiospecific Synthesis of (±)-Decarbomethoxyaklavinone," *Tetrahedron Lett.*, 22, 1981, 1779-1782.
McOmie, J.F.W., et al., "3,3"-Dihydroxybiphenyl," *Org. Synth., Collect.* vol. V, 1973, 412-414.
Mueller, B. et al., "RHO Kinase, a Promising Drug Target for Neurological Disorders," *Nature Reviews Drug Discovery*, 4, 2005, 387-398.
Newman, M.S. et al., "The Conversion of Phenols to Thiophenols via Dialkylthiocarbamates," *J. Org. Chem.* 31, 1966, 3980-3984.
Robinson, Richard A., "1-Dialkylaminoalkylaminoisoquinolines," *J. Am. Chem. Soc.*, 69, 1947, 1939-1942.
Wisniewski, K. et al., "Applications of the Mitsunobu Reaction in Peptide Chemistry," *J.Pept. Sc.* 4, 1998, 1-14.
Wolfe, J.P., et al., "Simple, Efficient Catalyst System for the Palladium-Catalyzed Amination of Aryl Chlorides, Bromides, and Triflates," *J. Org. Chem.* 65, 2000, 1158-1174.
Takami, A. et al., "Design and Synthesis of Rho Kinase Inhibitors (I)", *Bioorganic & Medicinal Chemistry*, 12(9):2115-2137; XP002309639; ISSN: 0968-0896; Elsevier Science Ltd. GB; (May 1, 2004).
Written Opinion dated Mar. 1, 2007 for International Application No. PCT/EP2006/069392 and International Search Report dated Mar. 1, 2007 for International Application No. PCT/EP2006/069392.

* cited by examiner

*Primary Examiner*—Zinna N Davis
(74) *Attorney, Agent, or Firm*—Susan Hess

(57) ABSTRACT

The invention relates to isoquinoline derivatives having the general Formula I

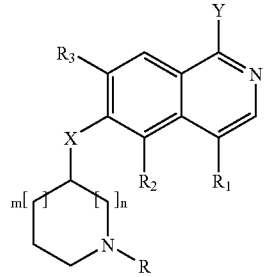

Formula I wherein X is O, S or NH; Y is OH or $NH_2$; m is 0, 1 or 2; n is 1 or 2; $R_1$ is H, when Y is $NH_2$; or $R_1$ is H, $(C_{1-4})$alkyl or halogen, when Y is OH; $R_2$ and $R_3$ are independently H, $(C_{1-4})$alkyl or halogen; R is H or $(C_{1-6})$alkyl, optionally substituted with OH, $(C_{1-4})$-alkyloxy, $(C_{1-4})$alkyloxycarbonyl, $(C_{3-7})$cycloalkyl, which may optionally comprise a heteroatom selected from O and S, $(C_{6-10})$aryl, $(C_{6-10})$aryloxy or a 5- or 6-membered heteroaryl group comprising 1-3 heteroatoms independently selected from O, N and S, each aryl or heteroaryl group being optionally substituted with 1-3 substituents independently selected from $(C_{1-4})$alkyl, $(C_{1-4})$alkyloxy, $(C_{1-4})$alkylsulfonyl and halogen; or a pharmaceutically acceptable salt thereof, to pharmaceutical compositions comprising the same as well as to the use of the isoquinoline derivatives in the treatment of ROCK-I related disorders such as hypertension, atherosclerosis and glaucoma.

10 Claims, No Drawings

ISOQUINOLINE DERIVATIVES

This invention relates to isoquinoline derivatives, to pharmaceutical compositions comprising the same, as well as to the use of these derivatives for the preparation of a medicament for the treatment of ROCK-I related disorders.

The vast majority of signal transduction pathways are controlled by the reversible phosphorylation of proteins. There are currently approximately 500 known protein kinases, which are responsible for phosphorylation of proteins and thus the control of cellular signalling events. Many diseases are associated with abnormal cellular responses triggered by protein kinase-mediated events and there has been a substantial effort in medicinal chemistry to find protein kinase inhibitors that are effective as therapeutic agents. The protein kinase family is classified into tyrosine kinases and serine/threonine kinases, based on the amino acid residue they phosphorylate. Recently, histidine kinases (which phosphorylate the imidazole nitrogen on a histidine residue) have also been discovered.

The AGC sub-family of kinases belong to the serine and threonine family of kinases and participate in a variety of signalling processes. This sub-family include Rho-associated coiled coil forming protein kinase (ROCK). Two ROCK isoforms have been reported: ROCK-I/ROKβ/p160ROCK and ROCKII/ROKχ/ Rho-kinase. These two proteins share 65% similarity at the amino-acid level and 92% in their kinase domains. ROCK-I and ROCK-II were among the first effectors of the small GTPases of the Rho family to be discovered. The Rho-ROCK signalling pathway controls cell shape adhesion, contractility, cell motility and invasion. First generation inhibitors Y-27632 and Fasudil have been used extensively to elucidate the biological roles of ROCK-I and ROCK-II in various diseases and or disorders. As a result, ROCK inhibitors have been suggested to have therapeutic value in bronchial asthma, cerebral vasospasm, coronary vasospasm, erectile dysfunction, glaucoma, preterm labour, vascular smooth muscle proliferation, myocardial hypertrophy, malignoma, ischemia/reperfusion-induced injury, endothelial dysfunction, Crohn's disease and colitis, neurite outgrowth, Raynaud's Disease, angina, Alzheimer's diseases, benign prostatic hyperplasia, cancer, neuropathic pain, hypertension and atherosclerosis (Mueller B. K et al, *Nature Reviews Drug Discovery* 4, 387-398 (2005); Hirooka Y. and Shimokawa H. *Am. J. Cardiovasc. Drugs* 5(1), 31-39 (2005); Hu E. and Lee D. *Current Opinion Ther. Targets* 9(4), 715-736 (2005)).

5-Substituted isoquinoline derivatives have been disclosed as inhibitors of the Rho/Rho kinase pathway in the International Patent Application WO 2004/00955 (EP 1541559; Asahi Kasei Pharma Corporation). N-substituted 5-isoquinolylamine derivatives were disclosed as Rho kinase inhibitors in the International Patent Application WO 2004/024717 (EP 1550660; Kirin Brewerey Kabashiki Kaisha). There remains a need for additional compounds useful in the treatment of Rho kinase mediated diseases such as hypertension, atherosclerosis and glaucoma.

To that aim the present invention provides isoquinoline derivatives having the general Formula I

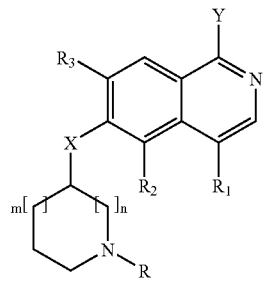

Formula I wherein
X is O, S or NH;
Y is OH or $NH_2$;
m is 0, 1 or 2;
n is 1 or 2;
$R_1$ is H, when Y is $NH_2$; or $R_1$ is H, $(C_{1-4})$alkyl or halogen, when Y is OH;
$R_2$ and $R_3$ are independently H, $(C_{1-4})$alkyl or halogen;
R is H or $(C_{1-6})$alkyl, optionally substituted with OH, $(C_{1-4})$alkyloxy, $(C_{1-4})$alkyloxycarbonyl, $(C_{3-7})$cycloalkyl, which may optionally comprise a heteroatom selected from O and S, $(C_{6-10})$aryl, $(C_{6-10})$aryloxy or a 5- or 6-membered heteroaryl group comprising 1-3 heteroatoms independently selected from O, N and S, each aryl or heteroaryl group being optionally substituted with 1-3 substituents independently selected from $(C_{1-4})$alkyl, $(C_{1-4})$alkyloxy, $(C_{1-4})$alkylsulfonyl and halogen; or a pharmaceutically acceptable salt thereof, which can be used in the treatment of Rho kinase mediated diseases such as hypertension, atherosclerosis and glaucoma.

The term $(C_{1-6})$alkyl as used in the definition of Formula I means a branched or unbranched alkyl group having 1-6 carbon atoms, like hexyl, pentyl, butyl, isobutyl, tertiary butyl, propyl, isopropyl, ethyl and methyl.

The term $(C_{1-4})$alkyl as used in the definition of Formula I means a branched or unbranched alkyl group having 1-4 carbon atoms, like butyl, isobutyl, tertiary butyl, propyl, isopropyl, ethyl and methyl.

The term $(C_{3-7})$cycloalkyl means a cycloalkyl group having 3-7 carbon atoms, like cycloheptyl, cyclohexyl, cyclopentyl, cyclobutyl and cyclopropyl. The $(C_{3-7})$cycloalkyl group may further comprise a heteroatom selected from O and S, as exemplified in tetrahydropyranyl, tetrahydrofuranyl, tetrahydrothiopyranyl and tetrahydrothienyl.

In the terms $(C_{1-4})$alkyloxy, $(C_{1-4})$alkyloxycarbonyl and $(C_{1-4})$alkylsulfonyl, $(C_{1-4})$alkyl has the meaning as defined above.

The term halogen means F, Cl, Br or I.

The term $(C_{6-10})$aryl means phenyl or naphthyl.

In the definition of Formula I the 5- or 6-membered heteroaryl group comprising 1-3 heteroatoms independently selected from O, N and S, is exemplified by pyrrolyl, thienyl, furyl, oxazolyl, thiazolyl, pyridyl, pyrimidinyl, pyrazinyl. Specified 5- or 6-membered heteroaryl groups are 2-furyl, 3-furyl, oxazole-2-yl, oxazole-4-yl, oxazol-5-yl, thiazol-2-yl, thiazole-4-yl, thiazole-5-yl, isoxazole-3-yl, isoxazole4-yl, is6xazole-5-yl, 1,2,3-oxadiazole-4-yl, 1,2,3-oxadiazole-5-yl, 1,3,4-oxadiazole-2-yl, 1,3,4-oxadiazole-5-yl, 1,2,4-oxadiazole-3-yl and 1,2,4-oxadiazole-5yl.

In one embodiment of the invention isoquinoline derivatives are provided having the general Formula I

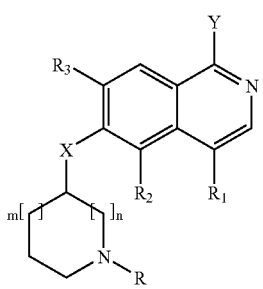

Formula I wherein
X is O, S or NH;
Y is OH or $NH_2$;
$R_1$ and $R_2$ are H;
$R_3$ is H or $(C_{1-4})$alkyl;
m is 0 or 1;
n is 1 or 2;
R is H or $(C_{1-4})$alkyl, optionally substituted with $(C_{3-7})$ cycloalkyl, which may optionally comprise a heteroatom selected from O and S, $(C_{6-10})$aryl or a 5- or 6-membered heteroaryl group comprising 1-3 heteroatoms independently selected from O, N and S, each aryl or heteroaryl group being optionally substituted with 1-3 substituents independently selected from $(C_{1-4})$alkyl, $(C_{1-4})$alkyloxy and halogen; or a pharmaceutically acceptable salt thereof There is a preference for isoquinoline derivatives of Formula I wherein Y is OH.

Further preferred compounds of Formula I are those wherein X is O.

In the more preferred compounds of the invention for Formula I, $R_3$ is independently H, methyl or halogen, $R_1$ and $R_2$ are H.

In further preferred compounds of the invention R represents H, $(C_{1-4})$alkyl, optionally substituted with phenyl or a 5- or 6-membered heteroaryl group comprising 1-3 hetero-atoms selected from O, N and S, the phenyl or heteroaryl group being optionally substituted with 1-3 substituents selected from $(C_{1-4})$alkyl, $(C_{1-4})$alkyloxy and one or more halogens.

Most preferred are the isoquinoline derivatives of Formula I wherein Y is OH, m is 1, n is 1 or 2, and R is H.

Specifically preferred isoquinoline derivatives of the invention are:
(S)-6-(piperidin-3-yloxy)-2H-isoquinolin-1-one;
(S)-7-methyl-6-(piperidin-3-yloxy)-2H-isoquinolin-1-one;
6-(perhydroazepin-4-yloxy)-2H-isoquinolin-1-one;
(S)-6-[1-(1H-pyrrol-2-ylmethyl)-piperidin-3-yloxy]-isoquinolin-1-ylamine;
(S)-6-[1-(4-methylbenzyl)piperidin-3-yloxy]isoquinolin-1-ylamine;
6-(piperidin-4-yloxy)-2H-isoquinolin-1-one;
(R)-6-(1-benzylpiperidin-3-yloxy)isoquinolin-1-ylamine;
6-[1-(2-phenoxyethyl)piperidin-3-yloxy]isoquinolin-1-ylamine;
(3S)-6-[1-(1-phenylethyl)piperidin-3-yloxy]isoquinolin-1-ylamine;
6-(piperidin-4-ylsulfanyl)-2H-isoquinolin-1-one;
6-(1-thiophen-2-ylmethylpiperidin-3-yloxy)isoquinolin-1-ylamine;
(S)-6-(1-benzylpiperidin-3-yloxy)isoquinolin-1-ylamine;
(R)-6-[1-(2-phenoxyethyl)piperidin-3-yloxy]-2H-isoquinolin-1-one;
(S)-6-[1-(4-fluorobenzyl)-piperidin-3-yloxy]-isoquinolin-1-ylamine;
(S)-4-bromo-6-(piperidin-3-yloxy)-2H-isoquinolin-1-one;
6-[1-(1H-pyrrol-2-ylmethyl)piperidin-4-yloxy]-2H-isoquinolin-1-one;
6-[1-(4-methoxybenzyl)piperidin-3-yloxy]-2H-isoquinolin-1-one;
(S)-6-[1-furan-3-ylmethylpiperidin-3-yloxy]isoquinolin-1-ylamine;
6-[1-phenethylpiperidin-3-yloxy]isoquinolin-1-ylamine;
6-[1-(3-methoxybenzyl)piperidin-4-yloxy]-2H-isoquinolin-1-one;
(S)-6-[1-(1H-pyrrol-3-ylmethyl)piperidin-3-yloxy]isoquinolin-1-ylamine;
(S)-6-[1-(2-oxo-2-phenylethyl)piperidin-3-yloxy]-2H-isoquinolin-1-one;
(S)-6-(pyrrolidin-3-yloxy)-2H-isoquinolin-1-one;
6-(1-cyclohexylmethylpiperidin-3-yloxy)-2H-isoquinolin-1-one;
6-(piperidin-3-ylsulfanyl)isoquinolin-1-ylamine;
6-(1-furan-2-ylmethylpiperidin-4-yloxy)-2H-isoquinolin-1-one;
(R)-6-(pyrrolidin-3-ylsulfanyl)isoquinolin-1-ylamine;
(S)-4-methyl-6-(piperidin-3-yloxy)-2H-isoquinolin-1-one;
(S)-6-(pyrrolidin-3-ylsulfanyl)isoquinolin-1-ylamine;
6-(1-methylpiperidin-4-yloxy)-2H-isoquinolin-1-one;
(S)-6-(piperidin-3-yloxy)-isoquinolin-1-ylamine;
6-(piperidin-4-ylsulfanyl)isoquinolin-1-ylamine;
(R)-6-(piperidin-3-yloxy)-2H-isoquinolin-1-one;
(S)-6-[1-(2-phenoxyethyl)piperidin-3-yloxy]-2H-isoquinolin-1-one;
6-(1-benzylpiperidin-3-yloxy)-7-methylisoquinolin-1-ylamine;
6-[1-(3-hydroxypropyl)piperidin-4-yloxy]-2H-isoquinolin-1-one;
6-[1-(2-hydroxyethyl)piperidin-4-yloxy]-2H-isoquinolin-1-one;
(R)-6-(pyrrolidin-3-yloxy)-2H-isoquinolin-1-one;
6-[1-(3-methylbenzyl)piperidin-4-yloxy]-2H-isoquinolin-1-one;
7-methyl-6-[1-(4-methylbenzyl)piperidin-3-yloxy]isoquinolin-1-ylamine;
(S)-5-bromo-6-(piperidin-3-yloxy)-2H-isoquinolin-1-one;
6-[1-(4-methoxybenzyl)piperidin-4-yloxy]-2H-isoquinolin-1-one, and pharmaceutically acceptable salts thereof.

Compounds of Formula I may be prepared from a compound of Formula II, wherein Y, X, $R_1$, $R_2$, $R_3$, n and m have the previously defined meaning, any reactive group in Y and X optionally carrying a protecting group, and Pg is an N-protecting group, by removal of said N-protecting group (Pg) and subsequent N-alkylation with an appropriate halide of Formula R-Hal, or reductive amination with an appropriate aldehyde derived from group R, after which any remaining protecting group is removed.

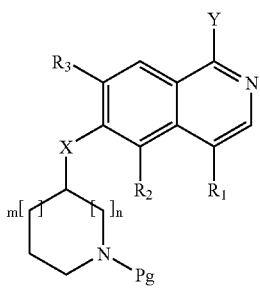

The term N-protecting group means a group commonly used for the protection of an amino group, like the alloxycarbonyl (Alloc) group, the tert-butyloxycarbonyl (Boc) group, the benzyloxycarbonyl (Z) group or the 9-fluorenylmethyloxycarbonyl (Fmoc) group. Removal of the protecting groups can take place in different ways, depending on the nature of those protecting groups. An overview of amino protecting groups and methods for their removal is given in T. W. Greene and P. G. M. Wuts, Protective Groups in Organic Synthesis, 2$^{nd}$ edition, 1991, John Wiley & Sons, Inc.

Compounds of Formula I and II wherein X is O or S can be prepared from the coupling of a compound of Formula III, wherein Y, X, $R_1$, $R_2$ and $R_3$ have the meaning as previously defined, with a compound of Formula IV, wherein n, m and R have the meaning as previously defined or Formula V, wherein n, m and Pg have the meaning as previously defined, and wherein L is OH, using standard Mitsunobu conditions (R. L. Elliot, H. Kopecka, D. E. Gunn, H. N. Lin and D. S. Garvey, *Bioorg. Med. Chem. Lett.*, 6, 2283 (1996); K. Wisniewski, A. S. Koldziejczyk and B. Falkiewicz, *J. Pept. Sc.* 4, 1 (1998).

Alternatively, Williamson $S_N2$ mediated displacement of a suitable leaving group of Formula IV or Formula V (were L=OMs, OTs- I, Br or Cl) using phenols or thiols of Formula III (where X=O or S) and an appropriate base can also be employed.

Compounds of Formula I where X=S, are prepared by Williamson $S_N2$ mediated displacement of a suitable leaving group of Formula IV or Formula V (were L=OMs, OTs, I, Br or Cl) using an appropriate base. The thiols of Formula III (where X=S) were prepared by treating the phenol of Formula III (where X=O and Y=OH or an amino group protected as a urethane such as Alloc, phthaloyl or amide such a benzoyl) with dimethylthiocarbamoyl chloride to give the corresponding O-ester. Newman-Karnes (Newman, M. S. and Karnes, H. A. *J. Org. Chem.* 1966, 31, 3980) conversion of the O-ester to the S-ester was accomplished using microwave irradiation. Subsequent hydrolysis of the S-ester gave thiols of Formula III (where X=S and Y=OH or an amino group protected as a urethane such as Alloc, phthaloyl or amide such a benzoyl).

Compounds of Formula I wherein X=NH can be prepared by conversion of the phenolic OH in compounds of Formula III to the corresponding bromide, which is subsequently coupled to an amine derivative of Formula V (L=NH$_2$) by a palladium-catalyzed amination reaction (Wolfe J. P., Tomori H, Sadighi J. P., Yin, J and Buchwald S. L. *J. Org. Chem.* 2000, 65, 1158-1174).

Demethylation of methyl aryl ethers of Formula VI (where Y=OH or NH$_2$) to the corresponding phenolic compounds of Formula III (where X=O and Y=OH or NH$_2$) may be accomplished by reaction with BBr$_3$ [J. F. W. McOmie and D. E. West, Org. Synth., Collect. Vol. V, 412 (1973)] or EtSNa [A. S. Kende and J. P. Rizzi, Tetrahedron Lett., 22, 1779 (1981)] or HBr.

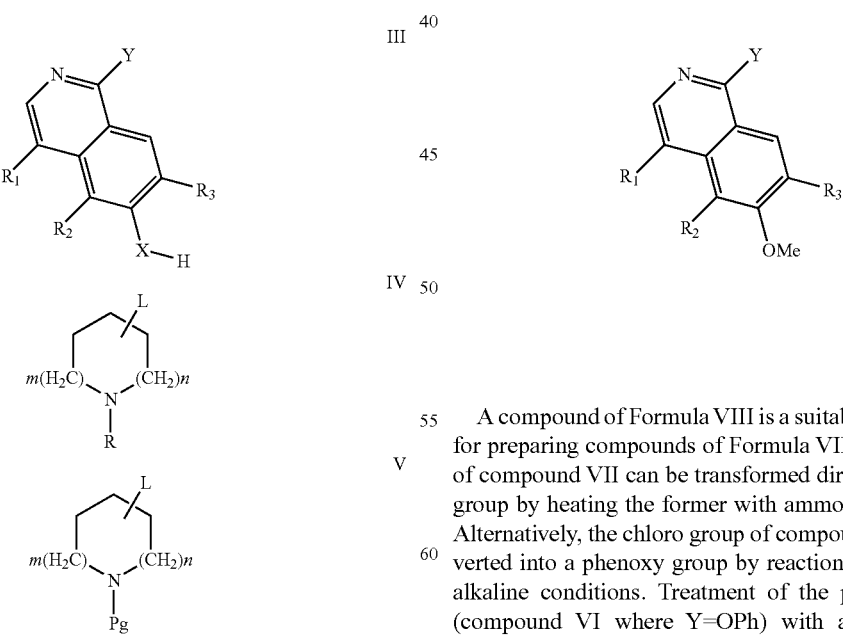

A compound of Formula VIII is a suitable starting material for preparing compounds of Formula VII. The chloro group of compound VII can be transformed directly into an amine group by heating the former with ammonia under pressure. Alternatively, the chloro group of compound VII can be converted into a phenoxy group by reaction with phenol under alkaline conditions. Treatment of the phenoxy derivative (compound VI where Y=OPh) with ammonium acetate affords the amine derivative of Formula VI (Y=NH$_2$). Compound VI (Y=NH$_2$) can also be obtained by treatment of compound VII with sodium azide and subsequent reduction of the aryl azide with PPh$_3$.

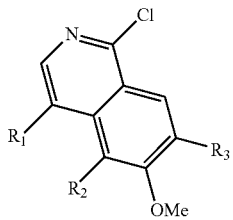

VII

Compound VII can be obtained from compound VIII by treatment with phosphorous oxychloride. Compound VII can also be prepared by converting 6-methoxyisoquinoline (Hendrickson, J. B.; Rodriguez, C.; *J. Org. Chem.* 1983, 48, 3344-3346) into the N-oxide salt, e.g. with a peracid, such as m-chloroperbenzoic acid, followed by HCl treatment, and subsequently reacting this N-oxide salt with a chlorinating reagent, like phosphoryl chloride (J. Robinson, *J. Am. Chem. Soc.*, 69,1941, 1939).

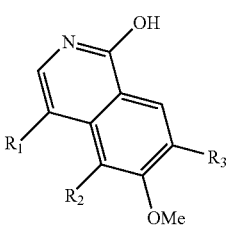

VIII

The 1-amino-6-bromoisoquinoline used in the preparation of compounds of Formula II wherein X=NH, Y=NH$_2$ and R$_1$-R$_3$ are H is prepared by Knoevenagel condensation of 3-bromobenzaldehyde to afford the 3-bromocinnamic acid. The acid is converted to the acyl chloride and then transformed into the acyl azide, which undergoes Curtius rearrangement on heating to afford the intermediate isocyanate. The intermediate isocyanate is heated further resulting in intramolecular ring closure to give 6-bromoisoquinolinone. Formation of the 1-amino-6-bromoisoquinoline can be accomplished using the same procedures described for compound VI (where Y=NH$_2$), using 1-chloro-6-bromoisoquinoline, which is generated by treatment of 6-bromoisoquinolinone with POCl$_3$.

Furthermore, preparation of compounds of Formula II wherein X=O, Y=NH$_2$ and R$_3$=methyl requires the 6-methoxy-7-methyl-isoquinolin-1-ylamine which is prepared using similar procedures as that for the 1-amino-6-bromoisoquinoline protocol above. In general compounds of Formula VI, wherein Y is OH, can be prepared from the corresponding cinnamic acids of Formula IX. The acids are converted to the acyl chlorides which are then transformed into the acyl azides of Formula X, which undergo Curtius rearrangement on heating to afford an intermediate isocyanates, which on further heating results in an intramolecular ring closure reaction to give an isoquinolinone of Formula VI.

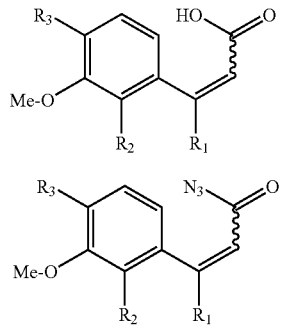

Formula IX

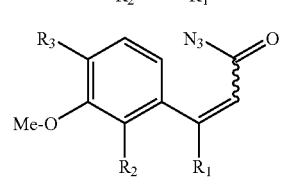

Formula X

Furthermore, compounds of Formula I and II (where Y=OH) can be converted into compounds of Formula I and II (where Y=NH$_2$) by treatment with POCl$_3$ followed by further treatment with ammonia.

Furthermore, compounds of Formula II, wherein Y is OH, R$_2$ and R$_3$ are H and R$_1$ is halogen can be prepared by halogenation with the appropriate N-halosuccinamide. Alternatively, compounds of Formula II, wherein Y is OH, X is O, R$_3$ and R$_2$ are H and R$_1$ is halogen can be prepared by halogenation under acidic conditions with the appropriate dihalogen (e.g. Br$_2$).

Furthermore, compounds of Formula VI, wherein Y is H, R$_1$ and R$_3$ are H and R$_2$ is Br can be prepared from 6-methoxyisoquinoline according to P. Chen et. al., *Bioorg. Med. Chem. Lett.* 13 (2003) 1345-1348. The corresponding bromide can be converted to the methyl derivative by transmetalation and subsequent reaction with a suitable electrophile such as iodomethane. Alternatively, the formyl or keto derivative may be formed from the suitable electrophile and subsequently reduced to the appropriate alkyl derivative. Alternatively, palladium-catalysed cross-coupling with organostannanes can be employed.

It is understood that compounds of the invention wherein Y is OH can also occur in the tautomeric amide O-form and may therefor also be described as 2H-isoquinolin-1-ones.

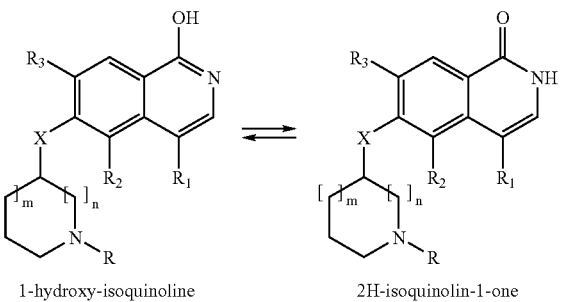

1-hydroxy-isoquinoline    2H-isoquinolin-1-one

The isoquinoline derivatives of Formula I and their salts may contain at least one centre of chirality, and exist therefore as stereoisomers, including enantiomers and diastereomers. The present invention includes the aforementioned stereoisomers within its scope and each of the individual R and S enantiomers of the compounds of Formula I and their salts, substantially free, i.e. associated with less than 5%, preferably less than 2%, in particular less than 1% of the other enantiomer, and mixtures of such enantiomers in any proportions including the racemic mixtures containing substantially equal amounts of the two enantiomers.

Methods for asymmetric synthesis or chiral separation whereby the pure stereoisomers are obtained are well known in the art, e.g. synthesis with chiral induction or starting from commercially available chiral substrates, or separation of stereoisomers, for example using chromatography on chiral media or by crystallisation with a chiral counter-ion.

Pharmaceutically acceptable salts of an isoquinoline derivative of the invention may be 25 obtained by treating a free base of a compound of Formula I with a mineral acid such as hydrochloric acid, hydrobromic acid, phosphoric acid and sulfuric acid, or an organic acid such as for example ascorbic acid, citric acid, tartaric acid, lactic acid, maleic acid, malonic acid, fumaric acid, glycolic acid, succinic acid, propionic acid, acetic acid and methane sulfonic acid.

The compounds of the invention may exist in unsolvated as well as in solvated forms with pharmaceutically acceptable solvents such as water, ethanol and the like. In general, the solvated forms are considered equivalent to the unsolvated forms for the purpose of the invention.

The isoquinoline derivatives of the present invention were found to possess inhibitory activity on recombinant human ROCK-1 in vitro, and are as such potentially useful in the treatment of ROCK-1 mediated diseases such as hypertension, atherosclerosis and glaucoma.

The present invention further provides pharmaceutical compositions comprising an isoquinoline derivative according to general Formula I, or a pharmaceutically acceptable salt thereof, in admixture with pharmaceutically acceptable auxiliaries, and optionally other therapeutic agents. The term "acceptable" means being compatible with the other ingredients of the composition and not deleterious to the recipients thereof. Compositions include e.g. those suitable for oral, sublingual, subcutaneous, intravenous, epidural, intrathecal, intramuscular, transdermal, pulmonary, local, or rectal administration, and the like, all in unit dosage forms for administration. A preferred route of administration is the oral route.

For oral administration, the active ingredient may be presented as discrete units, such as tablets, capsules, powders, granulates, solutions, suspensions, and the like. For parenteral administration, the pharmaceutical composition of the invention may be presented in unit-dose or multi-dose containers, e.g. injection liquids in predetermined amounts, for example in sealed vials and ampoules, and may also be stored in a freeze dried (lyophilized) condition requiring only the addition of sterile liquid carrier, e.g. water, prior to use.

Mixed with such pharmaceutically acceptable auxiliaries, e.g. as described in the standard reference, Gennaro, A. R. et al, Remington: *The Science and Practice of Pharmacy* (20th Edition, Lippincoft Williams & Wilkins, 2000, see especially Part 5: Pharmaceutical Manufacturing), the active agent may be compressed into solid dosage units, such as pills, tablets, or be processed into capsules, suppositories or patches. By means of pharmaceutically acceptable liquids the active agent can be applied as a fluid composition, e.g. as an injection preparation, in the form of a solution, suspension, emulsion, or as a spray, e.g. a nasal spray.

For making solid dosage units, the use of conventional additives such as fillers, colorants, polymeric binders and the like is contemplated. In general any pharmaceutically acceptable additive which does not interfere with the function of the active compounds can be used. Suitable carriers with which the active agent of the invention can be administered as solid compositions include lactose, starch, cellulose derivatives and the like, or mixtures thereof, used in suitable amounts. For parenteral administration, aqueous suspensions, isotonic saline solutions and sterile injectable solutions may be used, containing pharmaceutically acceptable dispersing agents and/or wetting agents, such as propylene glycol or butylene glycol.

The invention further includes a pharmaceutical composition, as hereinbefore described, in combination with packaging material suitable for said composition, said packaging material including instructions for the use of the composition for the use as hereinbefore described.

The compounds of the invention may be administered to humans in a sufficient amount and for a sufficient amount of time to alleviate the symptoms. Illustratively, dosage levels for humans can be in the range of 0.001-50 mg per kg body weight, preferably in-a dosage of 0.01-20 mg per kg body weight.

The invention is illustrated by the following examples.

General:

The following abbreviations are used:

Eluent: x-y % solvent A in solvent B means that a gradient of the eluent of x % (v/v) of solvent A in solvent B to y % (v/v) of solvent A in solvent B was used.

EXAMPLE 1

(S)-6-(1-Benzylpyrrolidin-3-yloxy)-isoquinolin-1-ylamine

1-Amino-6-hydroxyisoquinoline (50 mg, 0.312 mmol), prepared as described in WO 00/24718 (Akzo Nobel N.V.), and 2-tert-butylimino-2-diethylamino-1,3-dimethyl-perhydro-1,3,2-diazaphosphorine on polystyrene (284 mg, ~2.2 mmol.g$^{-1}$, ~0.624 mmol) were stirred at ambient temperature in acetonitrile (4 ml) for 15 min. (R) Methanesulfonic acid 1-benzylpyrrolidin-3yl ester (0.312 mmol) was added and the mixture heated to 110° C. and stirred for 60 h. The mixture was filtered and the precipitate washed with acetonitrile. The filtrate was concentrated and then purified by prep-HPLC to give (S)-6-(1-Benzylpyrrolidin-3-yloxy)-isoquinolin-1-ylamine (40 mg), El-MS: m/z=320.3 [M+H]$^+$.

EXAMPLE 2

(R)-6-(1-Benzylpyrrolidin-3-yloxy)-isoquinolin-1-ylamine

This compound was prepared from (S)-methanesulfonic acid 1-benzylpyrrolidin-3-yl ester and 1-amino-6-hydroxyisoquinoline by the procedure described in Example 1 to give the (R) 6-(1-benzylpyrrolidin-3-yloxy)-isoquinolin-1-ylamine product, El-MS: m/z=320.3 [M+H]$^+$.

EXAMPLE 3

(S)-6-(Piperidin-3-yloxy)-isoquinolin-1-ylamine

A: (R)-3-Hydroxy-piperidine-carboxylic acid tert-butyl ester

Di-tert-butyl dicarbonate (8.7 g, 11.6 mmol) was added to a suspension of (R)-3-hydroxypiperidine hydrochloride (5.0 g, 40.0 mmol) and sodium hydrogen carbonate (24.2 g, 29.0 mmol) in methanol (70 ml). Following the addition, the reaction was sonicated at ambient temperature for 1.5 hours during which time the temperature reached 40° C. The solvent was removed under reduced pressure and the crude material partitioned between ethyl acetate (200 ml) and water (200 ml). After separation of the layers, the organic was washed sequentially with sodium hydrogen carbonate (100 ml), water (100 ml), brine (100 ml) and water (100 ml) before being dried with magnesium sulphate and evaporated to dryness under reduced pressure. The (R)-3-hydroxy-piperidine carboxylic acid tert-butyl ester was obtained as colourless oil that solidified on standing.

B:
(R)-3-Methanesulfonyloxy-piperidine-1-carboxylic acid tert-butyl Ester

Methanesulfonyl chloride (1.73 ml, 22.5 mmol) was added to a cooled (ice bath, 0-4° C.), stirred solution of (R)-3-hydroxy-piperidine-carboxylic acid tert-butyl ester (3.0 g, 15 mmol) and triethylamine (3.12 ml, 22.5 mmol) in dichloromethane (30 ml). Following the addition the reaction was stirred at this temperature for 30 minutes before being allowed to warm to ambient temperature. After stirring at ambient temperature for 2 hours, aqueous sodium hydrogen carbonate (50 ml) was added, followed by vigorous stirring for 30 minutes. The reaction was diluted with dichloromethane (300 ml) and aqueous sodium hydrogen carbonate (300 ml) and after partitioning the organic phase was washed with water (200 ml), dried with magnesium sulphate and evaporated to dryness under reduced pressure to yield (R)-3-methanesulfonyloxypiperidine-1-carboxylic acid tert-butyl ester as a semi-crystalline solid.

C: (S)-3-(1-amino-isoquinolin-6-yloxy)piperidin-1-carboxylic acid tert-butyl Ester To a solution of (R)-3-hydroxypiperidine-1-carboxylic acid tert-butyl ester (209 mg, 1.04 mmol), triphenylphosphine (327 mg, 1.249 mmol), 1-amino-isoquinolin-6-ol (200 mg, 1.249 mmol) in THF (4 ml) and DMF (394 μL) at 0° C., under argon, was added dropwise diethylazodicarboxylate (197 mL) over 5 min. The mixture was warmed to ambient temperature and stirred for 48 h. Water was then added and the mixture basified with dilute NaOH. The mixture was extracted with ethyl acetate (X3), dried (sodium sulphate) filtered and evaporated under reduced pressure to give a residue. Flash chromatography of the residue on silica (eluent: 2-10% methanol in dichloromethane with 1% aqueous ammonia) gave (S) 3-(1-amino-isoquinolin-6-yloxy)piperidin-1--carboxylic acid tert-butyl ester (72 mg), El-MS: m/z=344.1 [M+H]$^+$.

For an alternate procedure for the preparation of (S)-3-(1-amino-isoquinolin-6-yloxy)piperidin-1-carboxylic acid tert-butyl ester, a suspension of 1-amino-6-hydroxyisoquinoline (0.8 g, 5.0 mmol), (R)-3-methanesulfonyloxypiperidine-1-carboxylic acid tert-butyl ester (1.76 g) and 2-tert-butyl-imino-2-diethylamino-1,3-dimethyl-perhydro-1,3,2-diazaphosphorine on polystyrene (3.4 g, ~2.2 mmol/g loading) in acetonitrile (10 ml) were heated at 160° C. over a period of 15 minutes using the microwave. The excess supported regent was removed by filtration, washing with acetonitrile followed by methanol, and the filtrate evaporated to dryness under reduced pressure. Purification was achieved by chromatography on silica (eluent: 2-10% methanol in ethyl acetate) to afford (S) 3-(1-amino-isoquinolin-6-yloxy)piperidin-1-carboxylic acid tert-butyl ester (72 mg), El-MS: m/z=344.1 [M+H]$^+$.

D: (S)-6-(Piperidin-3-yloxy)-isoquinolin-1-ylamine

A mixture of (S)-3-(1-amino-isoquinolin-6-yloxy)piperidin-1-carboxylic acid tert-butyl ester (72 mg) in dichloromethane (2 ml) and trifluoroacetic acid (1 ml) was stirred at ambient temperature for 1.5 h. The mixture was concentrated in vacuo then flash chromatography of the residue (eluent: 2-10% methanol in dichloromethane with 1% aqueous ammonia) gave (S)-6-(piperidin-3-yloxy)-isoquinolin-1-ylamine, El-MS: m/z=244.4 [M+H]$^+$.

EXAMPLE 4

6-(Piperidin-4-yloxy)-isoquinolin-1-ylamine

This compound was prepared from 4-hydroxypiperidine-1-carboxylic acid tert-butyl ester (455 mg, 2.26 mmol) and 1-amino-6-hydroxyisoquinoline (435 mg, 2.71 mmol) by the Mitsunobu procedure described in 3C. Subsequent Boc deprotection according to procedure described in 3D gave 6-(piperidin-4-yloxy)-isoquinolin-1-ylamine (140 mg), EIMS: m/z=244.6 [M+H]$^+$.

EXAMPLE 5

6-(Piperidin-3-yloxy)-isoquinolin-1-ylamine

This compound was prepared from racemic 3-hydroxypiperidine-1-carboxylic acid tert-butyl ester (207 mg, 1.02 mmol) and 1-amino-6-hydroxyisoquinoline (198 mg, 1.23 mmol) by the Mitsunobu procedure described in 3C, subsequent Boc deprotection according to procedure described in 3D gave racemic 6-(piperidin-3-yloxy)-isoquinolin-1-ylamine (30 mg), El-MS: m/z=244.4 [M+H]$^+$.

EXAMPLE 6

(S)-6-(Pyrrolidin-3-yloxy)-isoquinolin-1-ylamine

This compound was prepared from (S)-3-hydroxypyrrolidine-1-carboxylic acid tert-butyl ester (195 mg, 1.04 mmol) and 1-amino-6-hydroxyisoquinoline (200 mg, 1.25 mmol) by the Mitsunobu procedure described in 3C, subsequent Boc deprotection according to procedure described in 3D gave (S)-6-(pyrrolidin-3-yloxy)-isoquinolin-1-ylamine, El-MS: m/z=230.3 [M+H]$^+$.

Alternate Procedure

A solution of (R)-3-methanesulfonyloxypyrrolidine-1-carboxylic acid tert-butyl ester (2.95 g) in N, N-dimethylformamide (2 ml) was added dropwise to a stirred solution of 1-amino-6-hydroxyisoquinoline (1.2 g, 7.4 mmol) and K$_2$CO$_3$ (1.02 g, 7.4 mmol) in N, N-dimethylformamide (10 ml) at 100° C. The mixture was stirred for 1 h then cooled and water added. The mixture was acidified with glacial acetic acid then diluted with methanol. The mixture was loaded onto a pre-acidified SCX column using methanol and eluted with 2M ammonia in methanol to afford crude (S)-6-(pyrrolidin-3-yloxy)isoquinolin-1-ylamine, which was purified by flash chromatography on silica (eluent: 10% methanol in DCM with 1% ammonium hydroxide), El-MS: m/z=230.3 [M+H]$^+$.

EXAMPLE 7

(S)-6-(1-Benzylpiperidin-3-yloxy)isoquinolin-1-yl Amine

A: (S)-3-[1-(1,3-Dioxo-1,3-dihydroisoindol-2-yl) isoquinolin-6-yloxy]piperidine-1-carboxylic Acid Tert-butyl Ester To a solution of (S)-3-(1-amino-isoquinolin-6-yloxy)piperidin-1-carboxylic acid tert-butyl ester (380 mg, 1.11 mmol) and triethylamine (1.5 ml, 11.1 mmol) in anhydrous tetraydrofuran (1.5 ml) was added phthaloyl dichloride (170 μL, 1.16 mmol). The mixture was stirred at ambient temperature for 2 h and then poured into quickly stirring water. The mixture was extracted with dichloromethane (3×50 ml) and concentrated in vacuo to give a residue. Flash chromatography of the residue on silica (eluent: 0-100% ethyl acetate in heptane) gave (S)-3-[1-(1,3-dioxo-1,3-dihydroisoindol-2-yl)isoquinolin-6-yloxy]piperidine-1-carboxylic acid tert-butyl ester (390 mg) El1-MS: m/z=474.3 [M+H]+.

B: (S)-2-(6-piperidin-3-yloxy)isoquinolin-1-yl]isoindole-1.3-dione

A mixture of (S)-3-[1-(1,3-dioxo-1,3-dihydroisoindol-2-yl)isoquinolin-6-yloxy]piperidine-1-carboxylic acid tert-butyl ester (340 mg) in dichloromethane (14 ml) and trifluoroacetic acid (2.8 ml) was stirred at ambient temperature for 1 h. The mixture was concentrated in vacuo then flash chromatography of the residue on silica (eluent: 2-10% methanol in dichloromethane) gave (S)-2-(6-piperidin-3-yloxy)isoquinolin-1-yl]isoindole-1,3-dione (310 mg), EIMS: m/z=374.3 [M+H]+.

C: (S)-2-[6-(1-Benzylpiperidin-3-yloxy)isoquinolin-1-yl]isoindole-1,3-dione

To a solution of (S)-2-[6-piperidin-3-yloxy)isoquinolin-1-yl]isoindole-1,3-dione (30 mg, 62 μmol) in DMF (3 ml) was added potassium carbonate (10 mg, 74 μmol) and benzylbromide (9 μL, 74 μmol). The mixture was stirred for 4 h at ambient temperature, then the solvent removed in vacuo and water added. The mixture was extracted with dichloromethane, dried (magnesium sulphate) and concentrated in vacuo to give a residue. Flash chromatography of the residue on silica (eluent: 0-100% ethyl acetate in heptane) gave (S)-2-[6-(1-benzylpiperidin-3-yloxy)isoquinolin-1-yl]isoindole-1,3-dione, El-MS: m/z=464.3 [M+H]+.

D: (S)-6-(1-Benzylpiperidin-3-yloxy)isoquinolin-1-yl Amine

To a solution of the above (S)-2-[6-(1-benzylpiperidin-3-yloxy)isoquinolin-1-yl]-isoindole-1,3-dione (20 mg, 43 μmol) in ethanol (2 ml) was added hydrazine monohydrate (~3 μL, 65 μmol). The mixture was heated at 50° C. for 2 h then concentrated in vacuo to give a residue. The residue was purified by prep-HPLC to give (S)-6-(1-benzylpiperidine-3-yloxy)isoquinolin-1-yl amine El-MS: m/z=334.3 [M+H]+.

E: Alternate Procedure

A couple of drops of glacial acetic acid was added to a solution of racemic 6-(piperidin-3-yloxy)-isoquinolin-1-ylamine (52 mg, 0.214 mmol) and benzaldehyde (26 mL, 0.256 mmol) in acetonitrile (2 ml). The mixture was stirred for 20 minutes and then sodium triacetoxyborohydride (68 mg, 0.321 mmol) was added in portions. The mixture was stirred at ambient temperature for 20 h then concentrated in vacuo. The mixture was then partitioned between dichloromethane and saturated aqueous sodium hydrogencarbonate. The organic layer was separated then concentrated in vacuo to give a residue. The residue was purified by prep-HPLC to give 6-(1-benzylpiperidine-3-yloxy)isoquinolin-1-yl amine (73 mg) El-MS: m/z=334.3 [M+H]+.

The following compounds were prepared by the procedure as described in 7E using the appropriate aldehyde and racemic or enantiopure 6-(piperidin-3-yloxy)isoquinolin-1yl amine or 6-(pyrrolidin-3-yloxy)isoquinolin-1yl amine:

7F: 6-[1-(1H-Pyrrol-2-ylmethyl)piperidin-3-yloxy]isoquinolin-1-ylamine
Via 1H-Pyrrole-2-carbaldehyde: El-MS: m/z=323.5 [M+H]+.

7G: 6-(1-Thiophen-2-ylmethylpiperidin-3-yloxy)isoquinolin-1-ylamine Via Thiophene-2-carbaldehyde: El-MS: m/z=340.1[M+H]+.

7H: (S)-6-[1-(4-Fluorobenzyl)piperidin-3-yloxy]isoquinolin-1-ylamine
Via 4-Fluorobenzaldehyde: El-MS: m/z=352.5 [M+H]+.

7I: (S)-6-[1-Phenethylpiperidin-3-yloxy]isoquinolin-1-ylamine
Via Phenylacetaldehyde: El-MS: m/z=348.3 [M+H]+.

7J: (S)-6-[1-Furan-3-ylmethylpiperidin-3-yloxy]isoquinolin-1-ylamine
Via Furan-3-carbaldehyde: El-MS: m/z=324.5 [M+H]+.

7K: (S)-6-[1-(1 H-Pyrrol-2-ylmethyl)piperidin-3-yloxy]isoquinolin-1-ylamine
Via 1H-Pyrrole-2-carbaldehyde: El-MS: m/z=323.5 [M+H]+.

7L: (S)-6-[1-(1H-Pyrrol-3-ylmethyl)piperidin-3-yloxy]isoquinolin-1-ylamine
Via 1H-Pyrrole-3-carbaldehyde: El-MS: m/z=323.5 [M+H]+.

7M: (S)-6-[1-(3-Methylbenzyl)pyrrolidin-3-yloxy]isoquinolin-1-ylamine
Via 3-Methylbenzaldehyde: El-MS: m/z=334.5 [M+H]+.

7N: (S)-6-[1-(3-Fluorobenzyl)pyrrolidin-3-yloxy]isoquinolin-1-ylamine
Via 3-Fluorobenzaldehyde: El-MS: m/z=338.4 [M+H]+.

7O: (S)-6-[1-(4-Methanesulfonylbenzyl)pyrrolidin-3-yloxy]isoquinolin-1-ylamine
Via 4-Methanesulfonylbenzaldehyde: El-MS: m/z=398.4 [M+H]+.

7P: (S)-6-(1-Benzylpyrrolidin-3-yloxy)isoquinolin-1-ylamine
Via 1-Benzaldehyde: El-MS: m/z=320.1 [M+H]+.

7Q: (S)-6-[1-(3-Methoxybenzyl)pyrrolidin-3-yloxy]isoquinolin-1-ylamine
Via 3-Methoxybenzaldehyde: El-MS: m/z=350.5 [M+H]+.

7R: (S-6-[1-(1H-Pyrrol-3-ylmethyl)pyrrolidin-3-yloxy]isoquinolin-1-ylamine
Via 1H-Pyrrole-3-carbaldehyde: El-MS: m/z=309.4 [M+H]+.

7S: 6-(1-Furan-2-ylmethylpiperidin-3-yloxy)isoquinolin-1-ylamine
Via furan-2-carbaldehyde: El-MS: m/z=324.1 [M+H]+.

7T: 6-[1-(Tetrahydropyran-4-ylmethyl)piperidin-3-yloxy]isoquinolin-1-ylamine
Via tetrahydro-pyran-4-carbaldehyde: El-MS: m/z=341.9 [M+H]+.

7U: 6-[1-(4-tert-Butylbenzyl)-piperidin-3-yloxy]-isoquinolin-1-ylamine
Via 4-tert-Butylbenzaldehyde: El-MS: m/z=390.4 [M+H]+.

7V: (R-6-(1-Benzylpiperidin-3-yloxy)isoquinolin-1-ylamine
Via 1-Benzaldehyde: El-MS: m/z=334.3 [M+H]+.

EXAMPLE 8

The following compounds were prepared by the procedure as described in 7C and 7D using the appropriately substituted benzylbromide:

8A: (S)-6-[1-(3,4-Dichlorobenzyl)piperidin-3-yloxy]isoquinolin-1-ylamine
Via 3,4-Dichlorobenzylbromide: El-MS: m/z=402.3 [M+H]+.

8B: (S)-6-[1-(4-Methylbenzyl)piperidin-3-yloxy]isoquinolin-1-ylamine
Via 4-Methylbenzylbromide: El-MS: m/z=348.5 [M+H]+.

EXAMPLE 9

6-[1-(3-Phenylpropyl)piperidin-3-yloxy]isoquinolin-1-ylamine

This compound was prepared by the procedure described in 7C and 7D using 3-phenylpropylbromide. El-MS: m/z=362.5 [M+H]+.

EXAMPLE 10

10A:
6-(1-Methylpiperidin-4-yloxy)isoquinolin-1-ylamine

Three drops of glacial acetic acid was added to a solution of 6-(piperidin-4-yloxy)-isoquinolin-1-ylamine (35 mg, 0.14 mmol) in N, N-dimethylformamide (1 ml), followed by addition of formaldehyde (37% aqueous solution, 200 mL). Sodium triacetoxyboro-hydride (150 mg) was added to the mixture, which was shaken for 72 h. Saturated aqueous sodium hydrogen carbonate was added and then the mixture acidified with acetic acid. The mixture was loaded onto a pre-acidified SCX column, washed with methanol and then eluted with 2M ammonia in methanol. The crude product was isolated and further purified using prep-HPLC to give 6-(1-methylpiperidin-4-yloxy)-isoquinolin-1-ylamine (19 mg), EIMS: m/z=258.5 [M+H]+

10B:
6-(1-Ethypipieridin-4-yloxy)isoquinolin-1-ylamine 6-(1-Ethylpiperidin-4-yloxy)isoquinolin-1-ylamine was prepared as above using acetaldehyde, EIMS: m/z=272.6 [M+H]+

EXAMPLE 11

6-(1-Benzylpiperidin-4-yloxy)isoquinolin-1-ylamine

A drop of glacial acetic acid was added to a solution of 6-(piperidin-4-yloxy)-isoquinolin-1-ylamine (20 mg, 0.082 mmol) in N, N-dimethylformamide (0.5 ml), followed by addition of benzaldehyde (20 mL). The mixture was then treated with sodium triacetoxyborohydride (50 mg) and shaken for 2 h. Water (0.5 ml) was added, the mixture was stirred overnight and then purified by prep-HPLC to give 6-(1-benzyl-piperidin-4-yloxy)-isoquinolin-1--ylamine (28 mg), El-MS: m/z=334.3 [M+H]+.

EXAMPLE 12

6-(Piperidin-3-ylsulfanyl)isoquinolin-1-ylamine

A: N-(6-Hydroxyisoquinolin-1-yl)-benzamide

Benzoic anhydride (10.27 g) was added to a solution of 1-aminoisoquinolin-6-ol (3.312 g) in pyridine (53 ml) at ambient temperature. The mixture was heated at 125° C. for 1 h, the pyridine was removed under reduced pressure and excess pyridine was removed by azeotroping with toluene (X2). Water was added and the mixture extracted with dichloromethane (X3), dried (sodium sulphate) and concentrated in vacuo to give a solid precipitate. Recrystallisation with dichloromethane-diethyl ether gave benzoic acid 1-benzylaminoisoqinolin-6-yl ester (6 g), EIMS: m/z=369.1 [M+H]+.

A solution of NaOH (981 mg) in water $H_2O$ (65 ml) was added to a solution of benzoic acid 1-benzylaminoisoqinolin-6-yl ester (6 g) in methanol (65 ml) and tetrahydrofuran (65 ml). The mixture was stirred for 1.5 h at ambient temperature and then the organics were removed in vacuo. The mixture was diluted with water then extracted with ethyl acetate (x1). The aqueous phase was then acidified with dilute hydrochloric acid (pH ~3.5). Addition of ethyl acetate resulted in a solid precipitate which was filtered and washed with cold MeOH then heptane to give N-(6-hydroxyisoquinolin-1-yl)-benzamide (3.6 g), EIMS: m/z=265.1 [M+H]+.

B: N-(6-Mercaptoisoquinolin-1-yl)-benzamide

To a solution of N-(6-hydroxyisoquinolin-1-yl)-benzamide (100 mg, 0.379 mmol), triethylamine (105 mL, 0.758 mmol) and pyridine (306 mL, 3.79 mmol) in anhydrous tetrahydrofuran (2 ml) was added N,N-dimethylthiocarbamoyl chloride (70 mg, 0.568 mmol) at 0° C., under nitrogen. The mixture was heated to 65° C. and stirred for 48 h. The organics were removed under reduced pressure and excess pyridine was removed by azeotroping with toluene (x 2). Saturated aqueous $NaHCO_3$ was added and the mixture was extracted with dichloromethane (x 2), dried (magnesium sulphate) and concentrated in vacuo to give a residue. Flash chromatography of the residue (eluent: 5-50% ethyl acetate in heptane) gave dimethylthiocarbamic acid O-(1-benzoylaminoisoquinolin-6-yl)ester (70 mg), EIMS: m/z=352.7 [M+H]+.

A solution of the dimethylthiocarbamic acid O-(1-benzoylaminoisoquinolin-6-yl)ester (70 mg, ) in o-dichlorobenzene (3 ml) was irradiated in a microwave at 230 ° C. for 30 min. Flash chromatography of the mixture (eluent: 5-50% ethyl acetate in heptane) gave dimethylthiocarbamic acid S-(1-benzoylaminoisoquinolin-6-yl)ester (70 mg), EIMS: m/z=352.7 [M+H]+.

A solution of NaOH (92 mg) in water $H_2O$ (1 ml) was added to a solution of dimethylthiocarbamic acid S-(1-benzoylaminoisoquinolin-6-yl)ester (70 mg) in MeOH (1 ml) and THF (1 ml). The mixture was stirred for 1 h at ambient temperature then for a further 1 h at 56° C. The organics were removed in vacuo then the mixture was diluted with water and acidified with dilute hydrochloric acid (pH ~3.5). The mixture was extracted with ethyl acetate (X3), dried (sodium sulphate) and concentrated in vacuo to give a residue. Flash chromatography of the residue (eluent: 1-5% ethyl acetate in heptane) gave N-(6-mercaptoisoquinolin-1-yl)-benzamide as a yellow residue (30 mg).

C: 6-(Piperidin-3-ylsulfanyl)isoquinolin-1-ylamine

Potassium carbonate (44 mg, 0.32 mmol) and 3-methanesulfonyloxypiperidine-1-carboxylic acid tert-butyl ester (70 mg, 0.264 mmol) were added to a solution of the above N-(6-mercaptoisoquinolin-1-yl)-benzamide residue in DMF (2 ml). The mixture was irradiated in a microwave at 160° C. for 600 s then concentrated in vacuo to give a residue. The residue was purified by preparative HPLC to give 3-(1-benzoylaminoisoquinolin-6yl-sulfanyl)piperidine-1--carboxylic acid tert-butyl ester (18 mg), EIMS: m/z=464.3 [M+H]+ and m/z=486.5 [M+Na]+.

Glacial acetic acid (2 ml) and 6M hydrochloric acid (4.25 ml) were added to the 3-(1-benzoylaminoisoquinolin-6ylsulfanyl)piperidine-1-carboxylic acid tert-butyl ester (18 mg, 0.039 mmol) and the mixture was refluxed for 24 h. The mixture was then concentrated in vacuo to give a residue. The residue was loaded onto a pre-acidified SCX column using methanol and then eluted with 2M ammonia in methanol to

EXAMPLE 13

13A: (S)-6-(Pyrrolidin-3-ylsulfanyl)isoquinolin-1-ylamine

This compound was prepared by the procedure described in 12C using (R)-3-Methanesulfonyloxy-pyrrolidine-1-carboxylic acid tert-butyl ester to give (S)-6-(pyrrolidin-3-ylsulfanyl)isoquinolin-1-ylamine, El-MS: m/z=246.4 [M+H]$^+$.

13B: (R)-6-(Pyrrolidin-3-ylsulfanyl)isoquinolin-1-ylamine

This compound was prepared by the procedure described in 12C using (S)-3-methanesulfonyloxy-pyrrolidine-1-carboxylic acid tert-butyl ester to give (R)-6-(pyrrolidin-3-ylsulfanyl)isoquinolin-1-ylamine, El-MS: m/z=246.4 [M+H]$^+$.

13C: 6-(Piperidin-4-ylsulfanyl)isoquinolin-1-ylamine

This compound was prepared by the procedure described in 12C using 4-methanesulfonyloxypiperidine-1-carboxylic acid tert-butyl ester to give 6-(piperidin-4-ylsulfanyl)isoquinolin-1-ylamine, El-MS: m/z=260.3 [M+H]$^+$.

EXAMPLE 14

6-(Piperidin-3-ylamino)isoquinolin-1-ylamine

To a degassed solution of 1-amino-6-bromoisoquinolin (554 mg), prepared as described in WO 98/47876 (Akzo Nobel N.V.), 3-aminopiperidine-1-carboxylic acid tert-butyl ester (823 mg), 2-(di-tert-butylphosphino)biphenyl and sodium tert-butoxide (367 mg) in dioxane (10 ml) under argon, was added tris(dibenzylidene-acetone)dipalladium (0). The mixture was further degassed with argon then heated at 120° C. for 90 minutes. The mixture was cooled to room temperature then diluted with methanol. The crude mixture was loaded onto a pre-acidified SCX column and the basic products eluted with 2M ammonia in methanol to give a crude residue (700 mg). The residue was purified by preparative HPLC to give 3-(1-aminoisoquinolin-6-ylamino)piperidin-1-carboxylic acid tert-butyl ester. A mixture of the 3-(1-aminoisoquinolin-6-ylamino)-piperidin-1-carboxylic acid tert-butyl ester in dichloromethane (6 ml) and trifluoroacetic acid (3 ml) were stirred at ambient temperature for 3 h. The mixture was concentrated then purified by preparative HPLC followed by loading onto a pre-acidified SCX column and the free base eluted with 2M ammonia in methanol to give 6-(piperidin-3-ylamino)-isoquinolin-1-ylamine, El-MS: m/z=243.7 [M+H]$^+$.

EXAMPLE 15

7-Methyl-6-(piperidin-3-yloxy)-isoquinolin-1-ylamine

A: 1-Amino-7-methyl-isoquinolin6-ol hydrobromide

A mixture of 3-methoxy-4-methylbenzaldehyde (19.3 g, 0.129 mol), carbomethoxy methylene triphenylphosphorane (51 g) in toluene (250 ml) was refluxed for 24 h. The mixture was quenched with aqueous ammonium chloride and extracted with ethyl acetate and concentrated in vacuo to give a residue. The residue was purified by flash chromatography using ethyl acetate-heptane (1:1) to give 3-(3-methoxy-4-methylphenyl)acrylic acid methyl ester (27 g, 0.126 mol). A mixture of 3-(3-methoxy4-methylphenyl)acrylic acid methyl ester (27 g), sodium hydroxide (14 g), water (70 ml), methanol (140 ml) and tetrahydrofuran (70 ml) was refluxed at 50° C. for 1 h. The mixture was concentrated in vacuo and then water added. The mixture was filtered and 5 M HCl was added until precipitation occurred. The mixture was filtered and the solid precipitate washed with water and dried in-vacuo to give 3-(3-methoxy-4-methylphenyl)acrylic acid (23.5 g, 0.122 mol). Toluene (750 ml) and thionyl chloride (11 ml) were subsequently added to 3-(3-methoxy-4-methylphenyl)acrylic acid (20 g, 0.104 mol) at room temperature. The suspension was refluxed for 2 h while vigorously stirring to give a clear slightly yellow solution. The reaction mixture was concentrated in vacuo, then toluene added and the mixture re-concentrated in vacuo to give 3-(3-methoxy4-methylphenyl)acryloyl chloride for use in the next step. The 3-(3-methoxy4-methylphenyl)acryloyl chloride was dissolved in acetone (800 ml). The resulting solution was added slowly (15 min) at 0° C. to a mixture of sodium azide (13 g) in water (100 ml) and acetone (100 ml) while vigorously stirring and cooling with an ice-bath. After addition was complete the reaction mixture was stirred at 0° C. for 90 minutes while vigorously stirring. The reaction mixture was then poured out on ice-water (300 ml). After stirring for 15 minutes the mixture was filtered and the solid residue washed with excess water. The remaining solid residue was dissolved in dichloromethane (45 ml). The liberated water was removed with a separatory funnel. The dichloromethane layer was dried with Na$_2$SO$_4$ and filtered to give a dichloromethane solution of 3-(3-methoxy4-methylphenyl)acryloyl azide for immediate use in the next step. The dichloromethane azide solution was added in portions (Carefully !) using a dropping funnel to preheated diphenyl ether (50 ml) at 150° C., while gently stirring, in a three-necked roundbottomed flask, equiped with a Dean-Stark trap. During the addition nitrogen gas evolution takes place under formation of the isocyanate. The added dichloromethane is evaporated and collected with the Dean-Stark trap. After the addition was complete (~30 min) and no gas evolution observed, the mixture was heated to reflux (~250° C.) while stirring (at ~200° C. no more dichloromethane is evaporated and the Dean-Stark trap is removed quickly). The reaction mixture is kept at ~250° C. for 1 h then cooled to 125° C. and poured out in a mixture of acetone and heptane (1:10) . A solid precipitated and this was filtered and dried in vacuo to give 6-methoxy-7-methyl-2H-isoquinolin-1-one (12 g, 63.49 mmol). A suspension of 6-methoxy-7-methyl-2H-isoquinolin-1-one (5 g, 26.45 mmol) was treated at room temperature with phosphorus oxychloride (22 ml). The mixture was heated at 100° C. for 1 h with stirring then concentrated in vacuo to give a residue. Toluene was added to the residue which was further concentrated in-vacuo to give a residue which was taken up in toluene and slowly added to saturated aqueous sodium carbonate. The toluene layer was then separated. The aqueous layer was further mixed and extracted with toluene. The combined toluene layers were dried (MgSO$_4$) and concentrated in vacuo to give a residue. The residue was triturated with diethyl ether then filtered and dried in vacuo to give 1-chloro-6-methoxy-7-methyl-isoquinoline (4 g, 19.32 mmol). A mixture of 1-chloro-6-methoxy-7-methyl-isoquinoline (9 g, 43.48 mol), phenol (16.3 g), potassium hydroxide (9.45 g) and xylene (100 ml) was refluxed for 4 days. The reaction mixture was poured out into aqueous sodium hydroxide (4 M) and the xylene layer separated. The aqueous layer was extracted twice with toluene. The combined organic layers were dried (Na$_2$SO$_4$) and concentrated in vacuo to give a residue. The residue was purified by flash chromatography using dichloromethane gave 6-methoxy-7-methyl-1-phenoxy-isoquinoline (9 g, 33.96 mmol). A mixture of the crude 6-methoxy-7-methyl-1-phenoxy-isoquinoline (9 g, 33.96 mmol) and ammonium acetate (26 g) was melted with stirring at 170° C. for 5 h. The mixture was partitioned between aqueous sodium hydroxide (2 M) and ethyl acetate. The phases were separated and the organic phase extracted with dilute aqueous hydrochloric acid. The acidic aqueous phase was neutralized to pH 12 using sodium hydroxide (2M), extracted with ethyl acetate, dried (MgSO$_4$) then dried in vacuo to give 6-methoxy-7-methyl-isoquinolin-1-ylamine (5.11 g, 27.18 mmol). A mixture of 6-methoxy-7-methyl-isoquinolin-1-ylamine (5.11 g, 27.18 mmol) and 48% aqueous hydrobromic acid (150 ml) was heated at 125° C. for 2 days. The mixture was concentrated in vacuo and triturated with diethyl ether, dried in vacuo to give 1-amino-7-methyl-isoquinolin-6-ol hydrobromide (5 g), EIMS: m/z=175.1 [M+H]$^+$ B: 7-Methyl-6-(piperidin-3-yloxy)-isoquinolin-1-ylamine To a solution of 3-hydroxypiperidine-1-carboxylic acid tert-butyl ester (231 mg, 1.15 mmol), triphenylphosphine (301 mg, 1.15 mmol), 1-amino-7-methylisoquinolin-6-ol (200 mg, 1.15 mmol) in DMF (5 ml) at 0° C., under argon, was added dropwise diethylazodicarboxylate (181 [μL, 1.15 mmol). The mixture was then warmed to ambient temperature and stirred for 24 h. Methanol was added and the mixture loaded onto a pre-acidified SCX column, washed with methanol and then eluted with 2M ammonia in methanol. The crude product was isolated and further purified using prep-HPLC to give 3-(1-Amino-7-methylisoquinolin-6-yloxy)piperidine-1-carboxylic acid tert-butyl ester. A mixture of the (3-(1-Amino-7-methylisoquinolin-6-yloxy)piperidine-1-carboxylic acid tert-butyl ester in dichloromethane (10 ml) and trifluoroacetic acid (3 ml) was stirred at ambient temperature overnight. The mixture was concentrated in vacuo to give a residue. The residue was loaded onto a pre-acidified SCX column, washed with methanol and then eluted with 2M ammonia in methanol. The crude product was isolated and further purified using prep-HPLC to give 7-methyl-6-(piperidin-3-yloxy)isoquinolin-1-ylamine, El-MS: m/z=258.3 [M+H]$^+$.

EXAMPLE 16

7-Methyl-6-(piperidin-4-yloxy)isoquinolin-1-ylamine

A suspension of 1-amino-7-methylisoquinolin4-ol (430 mg, 2.4 mmol), 4-methanesulfonyloxypiperidine-1-carboxylic acid tert-butyl ester (1.0 g) and K$_2$CO$_3$ (510 mg, 3.7 mmol) in anhydrous N, N-dimethylformamide (8 ml) were microwaved at 100° C. for 10 minutes. A further equivalent of 4-methanesulfonyloxypiperidine-1-carboxylic acid tert-butyl ester in N, N-dimethylformamide (4 ml) was added and the mixture microwaved at 100° C. for a further 10 minutes. The mixture was diluted with water, acidified with acetic acid and further diluted with methanol. The mixture was loaded onto a pre-acidified SCX column, washed with methanol and then eluted with 2M ammonia in methanol. The crude product was isolated and further purified using flash chromatography on silica (eluent: 9:1:0.1 dichloromethane : methanol :ammonium hydroxide) to afford 4-(1-amino-7-methylisoquinolin-6-yloxy)piperidine-1-carboxylic acid tert-butyl ester (327 mg). A mixture of the 4-(1-amino-7-methylisoquinolin-6-yloxy)-piperidine-1-carboxylic acid tert-butyl ester in dichloromethane (5 ml) and trifluoroacetic acid (2 ml) was stirred at ambient temperature overnight. The mixture was concentrated in vacuo to give a residue. The residue was loaded onto a pre-acidified SCX column, washed with methanol and then eluted with 2M ammonia in methanol to give 7-methyl-6-(piperidin-4-yloxy)isoquinolin-1-ylamine (270 mg), El-MS: m/z=258.4 [M+H]$^+$.

EXAMPLE 17

The following compounds were prepared by the procedure as described in Example 16 using the (R)- or (S)-3-methanesulfonyloxypyrrolidine-1-carboxylic acid tert-butyl ester:
17A: (R)-7-Methyl-6-(pyrrolidin-3-yloxy)isoquinolin-1-ylamine
  El-MS: m/z=244.1 [M+H]$^+$.
17B: (S)-7-Methyl-6-(pyrrolidin-3-yloxy)isoquinolin-1-ylamine
  El-MS: m/z=244.3 [M+H]$^+$.

EXAMPLE 18

18A: 6-(1-Benzylpiperidin-4-yloxy)-7-methylisoquinolin-1-ylamine

A couple of drops of glacial acetic acid was added to a solution of 7-methyl-6-(piperidin-4-yloxy)isoquinolin-1-ylamine (30 mg, 0.117 mmol) in N, N-dimethylformamide (1 ml), followed by addition of benzaldehyde (50 μL). The mixture was then treated with sodium triacetoxyborohydride (100 mg) and stirred for 2 h. Water (1 ml) was added, the mixture was stirred for 30 min and then purified by prep-HPLC to give 6-(1-benzyl-piperidin-4-yloxy)-7-methylisoquinolin-1-ylamine (24 mg), El-MS: m/z=348.3 [M+H]$^+$.
The following compounds were prepared by the procedure as described above using the appropriate aldehyde:
18B: 7-Methyl-6-(1-methylpiperidin4-yloxy)isoquinolin-1-ylalmine
  via formaldehyde: El-MS: m/z=272.3 [M+H]$^+$.
18C: 6-[1-(4-Chlorobenzyl)piperidin-4-yloxy]-7-methylisoquinolin-1-ylamine
  Via 4-Chlorobenzaldehyde: El-MS: m/z=381.9 [M+H]$^+$.
18D: 7-Methyl-6-[1-(4-methylbenzyl)piperidin-4-yloxy]isoquinolin-1-ylamineVia 4-methylbenzaldehyde: El-MS: m/z=362.3 [M+H]$^+$.

EXAMPLE 19

The following compounds were prepared by the procedure as described in Example 18 using 7-methyl-6-(piperidin-3-yloxy)isoquinolin-1-ylamine and the appropriate aldehyde:
19A: 6-(1-Benzylpiperidin-3-yloxy)-7-methylisoquinolin-1-ylamine
  Via 1-benzaldehyde: El-MS: m/z=348.0 [M+H]$^+$.
19B: 7-Methyl-6-[1-(4-methylbenzyl)piperidin-3-yloxy]isoquinolin-1-ylamine
  Via 4-methylbenzaldehyde: El-MS: m/z=362.3 [M+H]$^+$.

EXAMPLE 20

The following compounds were prepared by the procedure as described in Example 18 using (R)- or (S)-7-Methyl-6-(pyrrolidin-3-yloxy)isoquinolin-1-ylamine and benzaldehyde:
20A: (R)-6-(1-Benzylpyrrolidin-3-yloxy)-7-methylisoquinolin-1-ylamine
  El-MS: m/z=334.0 [M+H]$^+$.
20B: (S)-6-(1-Benzylpyrrolidin-3-yloxy)-7-methylisoquinolin-1-ylamine
  El-MS: m/z=334.3 [M+H]$^+$.

EXAMPLE 21

6-[1-(2-Phenoxyethyl)piperidin-3-yloxy]isoquinolin-1-ylamine

To a solution of 6-(piperidin-3-yloxy)isoquinolin-1-ylamine (30 mg, 123 μmol) in DMF (1 ml) was added potassium carbonate (18 mg, 129 μmol) followed by a solution of (2-bromoethoxy)benzene (26 mg, 129 μmol) in acetonitrile (0.5 ml). The mixture was stirred for 16 h at ambient temperature, then the solvent removed in vacuo and aqueous sodium hydrogen carbonate added. The mixture was extracted with chloroform/iso-propanol (3:1), dried (magnesium sulphate) and concentrated in vacuo to give a residue. The residue was purified by prep-HPLC to give 6-[1-(2-phenoxyethyl)piperidin-3-yloxy]-isoquinolin-1-ylamine (12.5 mg) El-MS: m/z=364.8 [M+H]$^+$.

The following compounds were prepared by the procedure as described above using the appropriate bromide or chloride and enantiopure or racemic 6-(piperidin-3-yloxy)isoquinolin-1-ylamine or 6-(pyrrolidin-3-yloxy)isoquinolin-1-ylamine:

21A: (S)-6-[1-(2-Phenoxyethyl)piperidin-3-yloxy]isoquinolin-1-ylamine was prepared from the procedure above using (S)-6-(Piperidin-3-yloxy)isoquinolin-1-ylamine. El-MS: m/z=364.6 [M+H]$^+$.

21B: 3-[3-(1-Aminoisoquinolin-6-yloxy)piperidin-1-yl]propan-1-ol
Via 3-bromo-propan-1-ol: El-MS: m/z=302.5 [M+H]$^+$.

21C: 6-[1-(2-Methoxyethyl)piperidin-3-yloxy]isoquinolin-1-ylamine
Via 1-bromo-2-methoxyethane: El-MS: m/z=302.5 [M+H]$^+$.

21D: [3-(1-Aminoisoquinolin-6-yloxy)piperidin-1-yl]acetic acid methyl ester Via bromo-acetic acid methyl ester: El-MS: m/z=316.3 [M+H]$^+$.

21E: 2-[3-(1-Aminoisoquinolin-6-yloxy)piperidin-1-yl]ethanol
Via 2-bromoethanol: El-MS: m/z=288.1 [M+H]$^+$.

21F: 6-(1-Thiazol4-ylmethylpiperidin-3-yloxy)isoquinolin-1-ylamine Via 4-chloromethylthiazole: El-MS: m/z=341.1 [M+H]$^+$.

21G: (S)-6-[1-(1-Phenylethyl)piperidin-3-yloxy]isoquinolin-1-ylamine
Via (1-bromoethyl)benzene: El-MS: m/z=348.1 [M+H]$^+$.

21H: (S)-2-[3-(1-Aminoisoquinolin-6-yloxy)pyrrolidin-1-yl]ethanol
Via 2-bromoethanol: El-MS: m/z=274.5 [M+H]$^+$.

EXAMPLE 22

6-(Piperidin-3-yloxy)-2H-isoquinolin-1-one

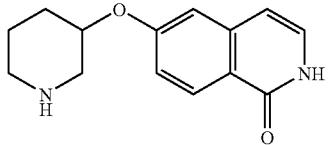

22A: 3-(1-chloroisoquinolin-6-yloxy)piperidine-1-carboxylic acid tert-butyl ester The 1-chloro-6-methoxyisoquinoline was prepared as described in WO 00/24718 (Akzo Nobel N.V.). Alternatively it can be prepared from 3-methoxybenzaldehyde using the same procedure as in Example 15A (for the synthesis of 1-chloro-6-methoxy-7-methyl-isoquinoline). The 1-chloro-6-methoxyisoquinoline is demethylated according to the procedure described in WO 00/24718 to afford 1-chloro-6-hydroxyisoquinoline. A suspension of 1-chloro-6-hydroxyisoquinoline (0.18 g, 1 mmol), 3-methanesulfonyloxy-piperidine-1-carboxylic acid tert-butyl ester (336 mg, 1.2 mmol) and 2-tert-butylimino-2-diethylamino-1,3-dimethyl-perhydro-1,3,2-diazaphosphorine on polystyrene (500 mg, ~2.2mmol/g loading) in acetonitrile (4 ml) were heated at 120° C. over a period of 900 seconds using the microwave. The excess supported reagent was removed by filtration, washing with methanol, and the filtrate evaporated to dryness under reduced pressure. Since the reaction had not gone to completion, the above procedure was repeated. Purification of the crude material was achieved by chromatography on silica (eluent: 0-25% ethyl acetate in heptane) to afford 3-(1-chloroisoquinolin-6-yloxy)piperidine-1-carboxylic acid tert-butyl ester (106 mg), El-MS: m/z=363.7 [M+H]$^+$.

22B: 6-(Piperidin-3-yloxy)2H-isoquinolin-1-one

Aqueous hydrochloric acid (5M, 2 ml) was added to a flask containing 3-(1-chloro isoquinolin-6-yloxy)piperidine-1-carboxylic acid tert-butyl (20 mg, 0.055 mmol) and the resulting solution stirred at ambient temperature for 5 h. The mixture was refluxed for 2 days then cooled to ambient temperature and loaded directly on to ion exchange column (SCX, 500 mg) following standard procedures to elute desired product as free base. The product was further purified by prep-HPLC to give 6-(piperidin-3-yloxy)-2H-isoquinolin-1-one (15.5 mg), El-MS: m/z=245.6 [M+H]$^+$.

EXAMPLE 23

6-(1-Benzyl-piperidin-3-yloxy)-2H-isoquinolin-1-one

23A: 1-Chloro-6-(piperidin-3-yloxy)-isoquinoline

Trifluoroacetic acid (1 ml) and dichloromethane (5 ml) were added to 3-(1-chloro-isoquinolin-6-yloxy)piperidine-1-carboxylic acid tert-butyl ester (370 mg) and the mixture stirred at ambient temperature for 48 h. The mixture was concentrated in vacuo then loaded onto a pre-acidified SCX column using methanol and eluted with 2M ammonia in methanol to afford 1-chloro-6-(piperidin-3-yloxy)isoquinoline (180 mg).

23B: 6-(1-Benzyl-piperidin-3-yloxy)-2H-isoquinolin-1-one

Sodium triacetoxyborohydride (100 mg, 3.9 mol eq) was added to a solution of 1-chloro-6-(piperidin-3-yloxy)isoquinoline (40mg), acetic acid (1 drops) and benzaldehyde (40 μl) in N, N-dimethylformamide (0.5 ml) and shaken for 17 hours. The reactions were quenched with water (0.5 ml) and shaken for 1 h then loaded onto a pre-acidified SCX column using methanol and eluted with 2M ammonia in methanol. The product was concentrated in vacuo to give a residue which was treated with 5M aqueous hydrochloric acid and heated in the microwave at 180° C. for 60 minutes. The mixture was concentrated in vacuo to give a residue which was purified by prep-HPLC to give 6-(1-benzylpiperidin-3-yloxy)-2H-isoquinolin-1-one, El-MS: m/z=335.7 [M+H]$^+$.

The following compounds were prepared by the procedure as described above using the appropriate aldehydes.

23C: 6-[1-(4-Fluorobenzyl)piperidin-3-yloxy]-2H-isoquinolin-1-one
Via 4-Fluorobenzaldehyde: El-MS: m/z=353.5 [M+H]+.
23D: 6-[1-(4-Methoxybenzyl)piperidin-3-yloxy]-2H-isoquinolin-1-one
Via 4-Methoxybenzaldehyde: El-MS: m/z=365.3 [M+H]+.

EXAMPLE 24

(S)-6-(piperidin-3-yloxy)-2H-isoquinolin-1-one

24A: 6-Hydroxy-2H-isoquinolin-1-one

1-Chloroisoquinolin-6-ol (5 g, 27.84 mmol) was mixed with hydrochloric acid (5M, 40 ml) and heated at 180° C. for 40 minutes under microwave conditions. The mixture was allowed to cool and then filtered. The brown solid was washed with diethyl ether and dried in vacuo at 50° C. to give 6-hydroxy-2H-isoquinolin-1-one, 4.45 g (98%), El-MS: m/z=162.4 [M+H]+.

24B: (R)-3-Methanesulphonyloxypiperidine-1-carboxylic acid tert-butyl ester

To a solution of (R)-3-hydroxypiperidine-1-carboxylic acid tert-butyl ester (6.51 g, 32.3 mmol) and triethylamine (6.8 ml, 1.5 mol eq) in dichloromethane (70 ml) at 0° C. was added a solution of methanesulphonyl chloride (3.73 ml, 1.5 mol) in dichloromethane (30 ml) over 30 minutes. The reaction was stirred at 0° C. for 2 hours. Saturated sodium hydrogen carbonate (100 ml) was added slowly. The organic phase was separated, washed with brine and dried over magnesium sulphate. Evaporation under reduced pressure yielded (R)-3-methanesulphonyloxypiperidine-1-carboxylic acid tert-butyl ester, 9.03 g (100%). NMR (CDCl$_3$ 7.27d) m 4.73(1H), m 3.63d(2H), m 3.44d(1H), m 3.32d (1H), s 3.05d(3H), m 1.95d (2H), m 1.83d(1 H), m 1.54d(1H), s 1.46d(9H)

24C: (S)-3-(Oxo-1,2- dihydroisoquinolin-6-yloxy) piperidine-1-carboxylic acid tert-butyl ester 6-Hydroxy-2H-isoquinolin-1-one (2 g, 12.41 mmol) and potassium carbonate (3.43 g, 2 mol) were mixed with N, N-dimethylformamide (40 ml) at 100° C. A solution of (R)-3-methanesulphonyloxypiperidine-1-carboxylic acid tert-butyl ester (5.2 g, 1.5 mol) in dimethylformamide (50 ml) was added dropwise over 15 minutes. The mixture was stirred at 100° C. for 3.5 hours and allowed to cool. The crude material was partitioned between ethyl acetate and water. The ethyl acetate layer was separated and washed with sodium hydroxide (2M) then brine and dried over magnesium sulphate. The residue was purified by flash chromatography on silica (eluent: 0-100% Heptane/Ethyl acetate followed by 5% 2M ammonia in methanol/ethyl acetate) to give (S)-3-(Oxo-1,2-dihydroisoquinolin-6-yloxy)-piperidine-1-carboxylic acid tert-butyl ester (1.25g, 29%), El-MS: m/z=345.3 [M+H]+.

24D: (S)-6-(Piperidin-3-yloxy)-2H-isoquinolin-1-one (S)-3-(Oxo-1,2-dihydroisoquinolin-6-yloxy)piperidine-1-carboxylic acid tert-butyl ester (1.25 g, 3.6 mmol) was mixed with dichloromethane (30 ml) and trifluoroacetic acid (10 ml) at ambient temperature for 15 minutes. Volatiles were removed under reduced pressure and excess trifluoroacetic acid was azeotroped with toluene. The residue was dissolved in methanol and purified using an SCX cartridge. Concentration gave (S)-6-(piperidin-3-yloxy)-2H-isoquinolin-1-one (450 mg, 51%), El-MS: m/z=245.4 [M+H]+.

The following compounds were prepared by the procedure described above using the appropriately synthesised mesylate.

24E: (R)-6-(Piperidin-3-yloxy)-2H-isoquinolin-1-one
Via (S)-3-methanesulphonyloxypiperidine-1-carboxylic acid tert-butyl ester: El-MS: m/z=245.3 [M+H]+.
24F: 6-(Piperidin4-yloxy)-2H-isoquinolin-1-one
Via 4-methanesulphonyloxypiperidine-1-carboxylic acid tert-butyl ester: El-MS: m/z=245.3 [M+H]+.
24G: (R)-6-(Pyrrolidin-3-yloxy)-2H-isoquinolin-1-one
Via (S)-3-methanesulphonyloxypyrrolidin-1-carboxylic acid tert-butyl ester: El-MS: m/z=231.1 [M+H]+.
24H: (S)-6-(Pyrrolidin-3-yloxy)-2H-isoquinolin-1-one
Via (R)-3-methanesulphonyloxypyrrolidin-1-carboxylic acid tert-butyl ester: El-MS: m/z=231.1 [M+H]+.
24I: 6-(Perhydroazepin-4-yloxy)-2H-isoquinolin-1-one
Via 4-methanesulphonyloxyperhydroazepin-1-carboxylic acid tert-butyl ester: El-MS: m/z=259.1 [M+H]+.

EXAMPLE 25

6-(Piperidin4-ylsulfanyl)-2H-isoquinolin-1-one

A: 6-mercapto-2H-isoquinolin-1-one

To a solution of 6-hydroxy-2H-isoquinolin-1-one (500 mg, 3.10 mmol), triethyl amine (860 μL, 6.2 mmol) and pyridine (2.5 ml, 31 mmol) in anhydrous tetrahydrofuran (16 ml) was added N, N-dimethylthiocarbamoyl chloride (573 mg, 4.65 mmol) at 0° C. The mixture was heated to 65° C. and stirred for 24 h. The mixture was concentrated in vacuo with the addition of toluene. Saturated aqueous NaHCO$_3$ was added to the residue and the mixture extracted with ethyl acetate (x3), dried (Na$_2$SO$_4$) and concentrated in vacuo to give a residue. Flash chromatography of the residue using ethyl acetate-heptane (5% to 100% ethylacetate) gave an unwanted side product (280 mg), followed by dimethylthiocarbamic acid 1-oxo-1,2-dihydroisoquinolin-6-yl ester (300 mg). A solution of the dimethylthiocarbamic acid 1-oxo-1,2-dihydroisoquinolin-6-yl ester in o-dichlorobenzene (2.5 ml) was heated under microwave conditions at 230° C. for 60 minutes. The mixture was loaded directly onto a column and flash chromatographed using ethyl acetate:heptane (1:9 to 99:1) to give dimethyl-thiocarbamic acid S-(1-oxo-1,2-dihydro-isoquinolin-6-yl) ester (140 mg). Methanol (7 ml) and potassium hydroxide (86 mg) were added to the dimethyl-thiocarbamic acid S-(1-oxo-1,2-dihydro-isoquinolin-6-yl) ester (140 mg) and the mixture refluxed, under nitrogen, for 2 h at 80° C. The mixture was then cooled and concentrated in vacuo to give a residue. Water was added and the mixture extracted with ethyl acetate (x2). The aqueous phase was acidified (pH ~2) using dilute hydrochloric acid and the mixture extracted with ethyl acetate (x3). The combined organics were dried (Na$_2$SO$_4$) and concentrated in vacuo to give crude 6-mercapto-2H-isoquinolin-1-one (104 mg).

B: 6-(piperidin-4-ylsulfanyl)-2H-isoquinolin-1-one

A mixture of 6-mercapto-2H-isoquinolin-1-one (50 mg, 0.28 mmol), 4-methane-sulphonyloxy-piperidine-1-carboxylic acid tert-butyl ester (117 mg, 0.42 mmol) and K$_2$CO$_3$ (64 mg, 0.46 mmol) in N, N-dimethylformamide (1.5 ml) was heated at 50° C. then left at ambient temperature overnight. Saturated aqueous sodium hydrogen carbonate was added to the mixture which was extracted with ethyl acetate (x 3). The combined organics were dried (Na$_2$SO$_4$) and concentrated in vacuo to give a residue. Flash chromatography of the residue using ethyl acetate:heptane (1:9 to 99:1) gave 4-(1-Oxo-1,2-dihydroisoquinolin-6-ylsulfanyl)piperidine-1-carboxylic acid tert-butyl ester (15 mg). A dichloromethane:trifluoroacetic acetic acid solution (7:3, 5 ml) was added to the 4-(1-Oxo-1,2-dihydroisoquinolin-6-ylsulfanyl)piperidine-1-carboxylic acid tert-butyl ester and the mixture stirred for 2 h, then concentrated in vacuo to give a residue. The residue was loaded onto a pre-acidified SCX column using methanol and eluted with 2M ammonia in methanol to afford crude 6-(piperidin-4-ylsulfanyl)-2H-isoquinolin-1-one, which was purified by prep-HPLC (2 mg), EI-MS: m/z=261.1 [M+H]$^+$.

EXAMPLE 26

(S)-7-Methyl-6-(Piperidin-3-yloxy)-2H-isoquinolin-1-one

26A: 6-Hydroxy-7-methyl-2H-isoquinolin-1-one

A mixture of 3-methoxy-4-methylbenzaldehyde (19.3 g, 0.129 mol), carbomethoxy methylene triphenylphosphorane (51 g) in toluene (250 ml) was refluxed for 24 h. The mixture was quenched with aqueous ammonium chloride and extracted with ethyl acetate and concentrated in vacuo to give a residue. The residue was purified by flash chromatography using ethyl acetate-heptane (1:1) to give 3-(3-methoxy4-methyl-phenyl)acrylic acid methyl ester (27 g, 0.126 mol). A mixture of 3-(3-methoxy4-methyl-phenyl)acrylic acid methyl ester (27 g), sodium hydroxide (14 g), water (70 ml), methanol (140 ml) and tetrahydrofuran (70 ml) was refluxed at 50° C. for 1 h. The mixture was concentrated in vacuo and then water added. The mixture was filtered and 5 M HCl was added until precipitation occurred. The mixture was filtered and the solid precipitate washed with water and dried in vacuo to give 3-(3-methoxy-4-methylphenyl)acrylic acid (23.5 g, 0.122 mol).

Toluene (750 ml) and thionyl chloride (11 ml) were subsequently added to 3-(3-methoxy-4-methylphenyl)acrylic acid (20 g, 0.104 mol) at room temperature. The suspension was refluxed for 2 h while vigorously stirring to give a clear slightly yellow solution. The reaction mixture was concentrated in vacuo, then toluene added and the mixture re-concentrated in vacuo to give 3-(3-methoxy-4-methylphenyl) acryloyl chloride for use in the next step.

The 3-(3-methoxy-4-methylphenyl)acryloyl chloride was dissolved in acetone (800 ml). The resulting solution was added slowly (15 min) at 0° C. to a mixture of sodium azide (13 g) in water (100 ml) and acetone (100 ml) while vigorously stirring and cooling with an ice-bath. After addition was complete the reaction mixture was stirred at 0° C. for 90 minutes while vigorously stirring. The reaction mixture was then poured out on ice-water (300ml). After stirring for 15 minutes the mixture was filtered and the solid residue washed with excess water. The remaining solid residue was dissolved in dichloromethane (45 ml). The liberated water was removed with a separatory funnel. The dichloromethane layer was dried with Na$_2$SO$_4$ and filtered to give a dichloromethane solution of 3-(3-methoxy-4-methylphenyl)acryloyl azide for immediate use in the next step.

The dichloromethane azide solution was added in portions (Carefully !) using a dropping funnel to preheated diphenyl ether (50 ml) at 150° C., while gently stirring, in a three-necked roundbottomed flask, equiped with a Dean-Stark trap. During the addition nitrogen gas evolution takes place under formation of the isocyanate. The added dichloromethane is evaporated and collected with the Dean-Stark trap. After the addition was complete (~30 min) and no gas evolution observed, the mixture was heated to reflux (~250° C.) while stirring (At ~200° C. no more dichloromethane is evaporated and the Dean-Stark trap is removed quickly). The reaction mixture is kept at ~250° C. for 1 h then cooled to 125° C. and poured out in a mixture of acetone and heptane (1:10). A solid precipitated and this was filtered and dried in vacuo to give 6-methoxy-7-methyl-2H-isoquinolin-1-one (12 g, 63.49 mmol).

A 1 M solution of boron tribromide (2.9 ml, 2.91 mmol) was added dropwise to a stirred suspension of 6-methoxy-7-methyl-2H-isoquinolin-1-one (100 mg, 0.53 mmol) in 1 ml of dichloromethane at 0-4° C. (ice bath). After stirring for 1 day at ambient temperature the reaction mixture was poured into ice and the pH was adjusted to 9 by adding concentrated aqueous ammonia. The precipitated material was collected by filtration, washed with water, and dried in vacuo to give 6-Hydroxy-7-methyl-2H-isoquinolin-1-one (51 mg, 55%), EI-MS: 176.6 [M+H]$^+$ 26B: (S)-7-Methyl-6-(piperidin-3-yloxy)-2H-isoquinolin-1-one

Prepared according to Example 24C and 24D using (R)-3-methanesulphonyloxy-piperidine-1-carboxylic acid tert-butyl ester and 6-hydroxy-7-methyl-2H-isoquinolin-1-one to afford 7-Methyl-6-(piperidin-3-yloxy)-2H-isoquinolin-1-one EI-MS: m/z=259.1 [M+H]$^+$.

EXAMPLE 27

(S)-4-Bromo-6-(piperidin-3-yloxy)-2H-isoquinolin-1-one

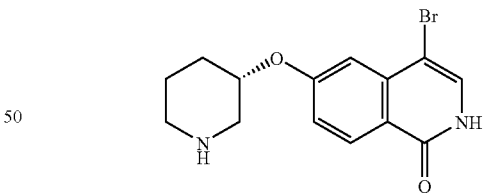

A solution of (S)-3-(oxo-1,2-dihydroisoquinolin-6-yloxy) piperidine-1-carboxylic acid tert-butyl ester (1 g, 2.9 mmol) and N-bromosuccinamide (516 mg, 2.9 mmol) in acetonitrile was stirred overnight at ambient temperature. The mixture was absorbed onto silica and flash chromatography (eluent: ethyl acetate) to give (S)-3-(4-bromo-1-oxo-1,2-dihydroisoquinblin-6-yloxy)piperidine-1-carboxylic acid tert-butyl ester (700 mg). Dichloromethane and trifluoroacetic acetic acid (3:1, 20 ml) were added to (S)-3-(4-bromo-1-oxo-1,2-dihydroisoquinolin-6-yloxy)piperidine-1-carboxylic acid tert-butyl ester and the mixture stirred for 2 h, then concentrated in vacuo to give a residue. The residue was loaded onto a pre-acidified SCX column using methanol and eluted with 2M ammonia in methanol to afford crude (S)-4-bromo-6-(piperidin-3-yloxy)-2H-isoquinolin-1-one (530 mg), which was purified by prep-HPLC, El-MS: m/z=325.5 [M+H]$^+$.

The following compounds were prepared by the procedure as described above using the appropriate building block.

27A: (R)-4-Bromo-6-(pyrrolidin-3-yloxy)-2H-isoquinolin-1-one

El-MS: m/z=309.3 and 311.0 [M+H]$^+$.

27B: (S)-4-Bromo-6-(pyrrolidin-3-yloxy)-2H-isoquinolin-1-one

El-MS: m/z=309.3 and 311.0 [M+H]$^+$.

EXAMPLE 28

(S)-4-Methyl-6-(piperidin-3-yloxy)-2H-isoquinolin-1-one

A: 3-(3-Methoxyphenyl)-but-2-enoic acid Methyl Ester 1-(3-Methoxyphenyl)ethanone (15 g, 0.1 mmol) and methyl(triphenylphosphoranylidene)acetate (62 g, 0.186 mmol) in toluene (75 ml) were heated at 100° C. for 2 days. After allowing cooling to ambient temperature the solvent was removed under reduced pressure to give crude product. Precipitation with EtOAc and heptane followed by flash chromatography of the concentrated mother liquor on silica (eluent: 20% EtOAc in heptane) afforded the product as a mixture of geometric isomers (21.8 g, 86%).

B: 3-(3-Methoxyphenyl)-but-2-enoic Acid 3-(3-Methoxy-phenyl)-but-2-enoic acid methyl ester (2 g, 7.9 mmol) and sodium hydroxide (0.78 g, 19.4 mmol) were dissolved in a mixture of water (50 ml), methanol (50 ml) and THF (50 ml). The mixture was stirred at ambient temperature for 16 hours and then concentrated under reduced pressure. The remaining aqueous solution was diluted with water and extracted with EtOAc twice. The aqueous was collected and acidified to pH 4 and extracted with EtOAc three times. The organics were combined, dried (magnesium sulphate) and concentrated in vacuo to give 3-(3-Methoxy-phenyl)-but-2-enoic acid as a white crystalline solid (1 g, 55%).

C: 6-Hydroxy-4-methyl-2H-isoquinolin-1-one

A solution of 3-(3-Methoxy-phenyl)-but-2-enoic acid (1.54 g, 7.8 mmol), diphenylphosphoryl azide (2.15 g) and triethylane (1.1 ml) in toluene was stirred at ambient temperature for 1 hour. The mixture was filtered through a silica plug, washing with toluene, and the filtrate concentrated under reduced pressure. The residue was dissolved in diphenylmethane (6 ml) and heated at 200° C. for 3 hours. After allowing cooling to room temperature, the solid precipitate was collected by filtration, washed with toluene and then dried to give 6-methoxy-4-methyl-2H-isoquinolin-1-one as a solid (0.22 g).

A suspension of 6-methoxy-4-methyl-2H-isoquinolin-1-one (215 mg, 1.1 mmol) in 5N hydrochloric acid (1 ml) was was irradiated in a microwave at 180° C. for 40 minutes. After removing solvent in vacuo the crude residue was purified by flash chromatography on silica (eluent: 1% methanol in DCM) to give 6-hydroxy-4-methyl-2H-isoquinolin-1-one (130 mg, 67%)., El-MS: m/z=174.3 [M-H]$^+$.

D: (S)-4-Methyl-6-(piperidin-3-yloxy)-2H-isoquinolin-1-one A suspension of 6-hydroxy-4-methyl-2H-isoquinolin-1-one (60 mg, 0.34 mmol) and potassium carbonate (70 mg, 0.51 mmol) in DMF (2.5 ml) was heated to 110° C. and a solution of (R)-3-methanesulfonyloxypiperidine-1-carboxylic acid tert-butyl ester (138 mg, 0.51 mmol) in DMF (1.5 ml) was added dropwise. Heating was continued at 110° C. for 16 hours and the solvent removed in vacuo. The residue was taken up in chloroform/isopropanol (3:1) and washed with aqueous sodium hydrogen carbonate. The organics were collected through a hydrophobic frit and concentrated to afford crude (S)-3-(4-methyl-1-oxo-1,2-dihydroisoquinolin-6-yloxy)piperidine-1-carboxylic acid tert-butyl ester.

The crude (S)-3-(4-Methyl-1-oxo-1,2-dihydroisoquinolin-6-yloxy)piperidine-1-carboxylic acid tert-butyl ester was dissolved in 2 ml of DCM and excess TFA added (0.2 ml). After stirring for 2 hours the solvent was removed under reduced pressure and the residue dissolved in methanol and partially purified by ion exchange chromatography. Further purification by prep-HPLC gave (S)-4-methyl-6-(piperidin-3-yloxy)-2H-isoquinolin-1-one, El-MS: m/z=259.1 [M+H]$^+$.

EXAMPLE 29

(S)-5-Bromo-6-(piperidin-3-yloxy)-2H-isoquinolin-1-one

A: 5-Bromo-6-hydroxy-2H-isoquinolin-1-one

To a solution of 6-methoxyisoquinoline (2.38 g, 14.9 mmol) in dichloromethane (55 ml) was added AlCl$_3$ (4.4 g, 33 mmol) under nitrogen at ambient temperature. The mixture was stirred for 30 min then Br$_2$ (0.92 ml, 18 mmol) was added at 0° C. The mixture was stirred for 2 h, then poured into water and neutralised with solid Na$_2$CO$_3$. The mixture was filtered through celite and the filtrate extracted with dichloromethane and chloroform. The combined organics were washed with brine, dried (Na$_2$SO$_4$) and concentrated in vacuo to give a residue. Flash chromatography of the residue on silica (eluent: 50-100% ethyl acetate in heptane) gave 5-bromo-6-methoxyisoquinoline (1.2 g, 34% yield).

m-Chloroperbenzoic acid (1.4 g, 75%) was added in portions to a stirred solution of 5-bromo-6-methoxyisoquinoline (12 g, 5.04 mmol) in dichloromethane (12 ml). The mixture was stirred for 1 h then further dichloromethane (10 ml) added and the mixture stirred for an additional 2 h. Methanol (12 ml) was added and the mixture concentrated in vacuo to ~9 ml, then 1M hydrochloric acid in diethyl ether (10 ml) was added. The mixture was diluted with ether and filtered, the precipitated solid was washed with diethyl ether and dried in vacuo to give crude 5-bromo-6-methoxyisoquinoline-N-oxide hydrochloride (1.22 g).

POCl$_3$ (6.5 ml) was added to the 5-bromo-6-methoxyisoquinoline-N-oxide hydrochloride (1.22 g) and the mixture heated at 90° C. for 6 h. Excess POCl$_3$ was removed in vacuo and the remaining solid washed with water, filtered and dried in vacuo to give 5-bromo-1-chloro-6-methoxyisoquinoline (1.26 g).

A solution of 1M BBr$_3$ in dichloromethane (25.5 ml) was added dropwise to a stirred solution of 5-bromo-1-chloro-6-methoxyisoquinoline (1.26 g) in dichloromethane at 10° C. The mixture was stirred at ambient temperature for 48 h then poured into ice-water and the pH adjusted to 8 by adding concentrated aqueous ammonia. The mixture was extracted with ethyl acetate (x 2) and the aqueous phase then acidified to pH ~4 using dilute hydrochloric acid. The aqueous phase was extracted with ethyl acetate (x 2), the combined organics were dried (Na$_2$SO$_4$) and concentrated in vacuo to give 5-bromo-1-chloro-6-hydroxyisoquinoline (1.1 g), El-MS: m/z=257.9, 260.0 and 261.6 [M+H]$^+$.

B: (S)-5-Bromo-6-(piperidin-3-yloxy)-2H-isoquinolin-1-one

5-Bromo-1-chloro-6-hydroxyisoquinoline (108 mg, 0.42 mmol) was mixed with hydrochloric acid (5M, 2 ml) and heated under microwave conditions at 150° C. for 40 minutes. The cooled residue was mixed with methanol and azeotroped to dryness under reduced pressure to give 5-bromo-6-hydroxy-2H-isoquinolin-1-one El-MS: m/z=240 and 242[M+H]$^+$.

The crude 5-bromo-6-hydroxy-2H-isoquinolin-1-one (93 mg) was mixed with (R)-3-methanesulphonyloxypiperidine-1-carboxylic acid tert-butyl ester (500 mg, 4.3 mol eq), potassium carbonate (700 mg, 12 mol eq) and N, N-dimethylformamide (2 ml). The mixture was microwaved at 150° C. for 20 minutes. Water was added to the mixture and the crude product extracted out into ethyl acetate. The organic phase was washed with brine and dried (MgSO$_4$). The organics were concentrated in vacuo then purified by prep-HPLC. Dichloromethane and trifluoroacetic acid (3:1, 2 ml) were added and the mixture stirred for 1 h then concentrated in vacuo to give a residue. The residue was loaded onto a pre-acidified SCX column using methanol and eluted with 2M ammonia in methanol to afford (S)-5-bromo-6-(piperidin-3-yloxy)-2H-isoquinolin-1-one. The residue was purified by prep-HPLC (1.8 mg), El-MS: m/z=323.5 and 323.5 [M+H]$^+$

EXAMPLE 30

30A: 6-[1-(4-Methylbenzyl)piperidin-4-yloxy]-2H-isoquinolin-1-one

Sodium triacetoxyborohydride (100 mg, 3.9 mol eq) was added to a solution of 6-(piperidin-4-yloxy)-2H-isoquinolin-1-one (30 mg, 0.12 mmol), acetic acid (2 drops) and 4-methylbenzaldehyde (50 μl or 50 mg) in N, N-dimethylformamide (700 μl) and shaken for 17 hours. The reaction was quenched with water and methanol and the product semi-purified using an SCX cartridge. The product was further purified by prep-HPLC to afford 6-[1-(4-Methylbenzyl)piperidin4-yloxy]-2H-isoquinolin-1-one: El-MS: m/z=349.4 [M+H]$^+$.

The following compounds were prepared by the procedure as described above using the appropriate aldehyde.
30B: 6-[1-(3-Methylbenzyl)piperidin-4-yloxy]-2H-isoquinolin-1-one
Via 3-Methylbenzaldehyde: El-MS: m/z=349.4 [M+H]$^+$.
30C: 6-[1-(4-Methoxybenzyl)piperidin-4-yloxy]-2H-isoquinolin-1-one
Via 4-Methoxybenzaldehyde: El-MS: m/z=365.1 [M+H]$^+$.
30D: 3-[4-(1-Oxo-1,2-dihydroisoquinolin-6-yloxy)piperidin-1-ylmethyl]benzonitrile
Via 3-Cyanobenzaldehyde:El-MS: m/z=360.5 [M+H]$^+$.
30E: 6-(1-Furan-2-ylmethylpiperidin-4-yloxy)-2H-isoquinolin-1-one
Via 1-Furan-2-carbaldehyde: El-MS: m/z=325.5 [M+H]$^+$.
30F: 6-(1-Furan-3-ylmethylpiperidin-4-yloxy)-2H-isoquinolin-1-one
Via 1-Furan-3-carbaldehyde: El-MS: m/z=325.5 [M+H]$^+$.
30G: 6-(1-Methylpiperidin-4-yloxy)-2H-isoquinolin-1-one
Via formaldehyde: El-MS: m/z=259.1[M+H]$^+$.
30H: 6-[1-(1H-pyrrol-3-ylmethyl)piperidin-4-yloxy]-2H-isoquinolin-1-one Via 1H-Pyrrol-3-carbaldehyde: El-MS: m/z=324.6 [M+H]$^+$.
30I: 6-(1-Benzylpiperidin-4-yloxy)-2H-isoquinolin-1-one
Via Benzaldehyde: El-MS: m/z=335.5 [M+H]$^+$.

EXAMPLE 31

31A: 6-[1-(2-Phenoxyethyl)piperidin-4-yloxy]-2H-isoquinolin-1-one

2-Phenoxyethyl bromide (1 mol eq) was added to a suspension of 6-(piperidin-4-yloxy)-2H-isoquinolin-1-one (30 mg, 0.12 mmol) and potassium carbonate (50 mgs, 3 mol) in N, N-dimethylformamide (1 ml) and shaken for 17 hours. The reactions was quenched with hydrochloric acid (2M) and methanol and passed down an SCX cartridge. The product was purified by preparative HPLC under basic conditions. The clean product was isolated by evaporation under reduced pressure to afford 6-[1-(2-phenoxyethyl)piperidin-4-yloxy]-2H-isoquinolin-1-one: El-MS: m/z=365.1 [M+H]$^+$.

The following compounds were prepared by the procedure as described above using the appropriate bromides:
31B: 6-[1-(2-Methoxyethyl)piperidin-4-yloxy]-2H-isoquinolin-1-one
Via 2-Methoxyethyl bromide: El-MS: m/z =303.1[M+H)]$^+$.
31C: 6-[1-(3-Hydroxypropyl)piperidin-4-yloxy]-2H-isoquinolin-1-one
Via 3-Hydroxypropyl bromide: El-MS: m/z=303.1[M+H]$^+$.
31D: 6-(1-Cyclopropylmethylpiperidin-4-yloxy)2H-isoquinolin-1-one
Via (bromomethyl)cyclopropyl: El-MS: m/z=299.5[M+H]$^+$.
31E: 6-[1-(2-Hydroxyethyl)piperidin-4-yloxy]-2H-isoquinolin-1-one
Via 2-bromoethanol: El-MS: m/z=289.3[M+H]$^+$.
31F: 6-[1-(3-Methoxybenzyl)piperidin-4-yloxy]-2H-isoquinolin-1-one
Via 3-Methoxybenzaldehyde: El-MS: m/z=365.5 [M+H]$^+$.
31G: 6-[1-(1 H-Pyrrol-2-ylmethyl)piperidin-4-yloxy]-2H-isoquinolin-1-one
Via 1H-Pyrrol-2-carbaldehyde: El-MS: m/z=324.5 [M+H]$^+$.

EXAMPLE 32

32A: (S) 6-[1-(2-Benzyloxyethyl)piperidin-3-yloxy]-2H-isoquinolin-1-one

2-Benzyloxyethyl bromide (1 mol) was added to a suspension of (S)-6-(piperidin-3-yloxy)-2H-isoquinolin-1-one (30 mg, 0.12 mmol) and potassium carbonate (70mg, 4.2 mol) in N, N-dimethylformamide (500 μl) and shaken for 17 hours. The reaction was quenched with hydrochloric acid (2M) and methanol and passed down an SCX cartridge. The products were purified by preparative HPLC under basic conditions. The clean products were isolated by evaporation under reduced pressure to afford (S)-6-[1-(2-benzyloxyethyl)piperidin-3-yloxy]-2H-isoquinolin-1-one: El-MS: m/z=379.4 [M+H]$^+$.

The following compounds were prepared by the procedure as described above using the appropriate bromides, (R)- or (S)-6-(piperidin-3-yloxy)-2H-isoquinolin-1-one and (R)-6-(pyrrolidin-3-yloxy)-2H-isoquinolin-1-one:
32B: (S)-6-[1-(2-Oxo-2-phenylethyl)piperidin-3-yloxy]-2H-isoquinolin-1-one
Via 2-bromideacetophenone: El-MS: m/z=363.5[M+H]$^+$.

32C: (S)-6-[1-(2-Phenoxyethyl)piperidin-3-yloxy]-2H-isoquinolin-1-one
Via beta-bromophenetole: El-MS: m/z=365.1 [M+H]⁺.

32D: (R)-6-[1-(3-Hydroxypropyl)pyrrolidin-3-yloxy]-2H-isoquinolin-1-one
Via 3-Hydroxypropyl bromide: El-MS: m/z=289.3 [M+H]⁺.

32E: (R)-6-[1-(2-Phenoxyethyl)piperidin-3-yloxy]-2H-isoquinolin-1-one
Via beta-bromophenetole: El-MS: m/z=365.5 [M+H]⁺.

EXAMPLE 33

33A:
6-(1-Ethylpiperidin-3-yloxy)-2H-isoquinolin-1-one

Sodium triacetoxyborohydride (45 mg, 1.8 mol) was added to a solution of 6-(piperidin-3-yloxy)-2H-isoquinolin-1-one (30 mg, 0.12 mmol), acetic acid (100 μl) and acetaldehyde (50 μl or 50 mg) in N, N-dimethylformamide (500 μl) and shaken for 17 hours. The reaction was quenched with water and methanol and passed down an SCX cartridge. The product was purified by preparative HPLC under basic conditions. The clean products were isolated by evaporation under reduced pressure to give 6-(1-ethyl-piperidin-3-yloxy)-2H-isoquinolin-1-one: El-MS: m/z=273.5[M+H]⁺.

The following compounds were prepared by the procedure as described above using the appropriate aldehyde, racemic or (R)-6-(piperidin-3-yloxy)-2H-isoquinolin-1-one and (R)-6-(pyrrolidin-3-yloxy)-2H-isoquinolin-1-one:

33B: 6-[1-(2-Ethylbutyl)piperidin-3-yloxy]-2H-isoquinolin-1-one
Via 2-ethylbutyraldehyde: El-MS: m/z=329.5[M+H]⁺.

33C: 6-(1-Cyclohexylmethylpiperidin-3-yloxy)-2H-isoquinolin-1-one
Via cyclohexanecarboxaldehyde: El-MS: m/z=341.1 [M+H]⁺.

33D: (R)-6-(1-Benzylpiperidin-3-yloxy)-2H-isoquinolin-1-one
Via Benzaldehyde: El-MS: m/z=335.5 [M+H]⁺.

33E: (R)-6-(1-Methylpyrrolidin-3-yloxy)-2H-isoquinolin-1-one
Via Formaldehyde: El-MS: m/z=245.6 [M+H]⁺.

EXAMPLE 34

In-Vitro Determination of Inhibitory Activity of Compounds of the Invention on Recombinant Human ROCK-1

To a 384 well microtitre plate is added 5 μl of a 250 μM solution of test compound in assay buffer (20 mM Hepes pH7.4, 0.01% tween) with 4% dimethylsulfoxide (DMSO), plus 5 μl of a mixture containing 100 nM fluorescein-labelled peptide (AKRRRLSSLRAK-fluorescein from the Peptide Institute, Japan), 20 μM ATP, 10 mM $MgCl_2$ diluted in assay buffer containing 2 mM dithiothreitol. 10 μl of a 0.1 ng/μl solution of recombinant human ROCK-1 in assay buffer containing 2 mM dithiothreitol, is then added to each well, yielding a final test compound concentration of 10 μM. Following a one hour incubation at room temperature in the dark, enzyme activity is detected by adding 60 μl of IMAP binding reagent (Molecular Devices) to each well. The plate is incubated for a further 30 minutes at room temperature in the dark and the resulting change in fluorescence polarisation is measured on the Analyst HT (Molecular Devices) at an excitation wavelength of 485 nM and emission wavelength of 530 nM. Percentage enzyme activity is calculated by comparison of this activity to that of a solution containing 30 μM Y-27632 from Tocris (generates maximum inhibition of ROCK-1 activity). Compounds are subsequently subjected to a dose response curve analysis in order to determine $IC_{50}$ values for active compounds (where $IC_{50}$ is the concentration of test compound causing 50% inhibition of the enzymatic activity). All exemplified compounds have $pIC_{50}$ values greater than 5.0. Preferred compounds of the invention are characterized by a pIC50>6.0. Table 1 shows the $pIC_{50}$ values obtained for some representative compounds of the invention.

TABLE I

| Compound | ROCK-I $pIC_{50}$ | Example |
|---|---|---|
| (S)-6-(piperidin-3-yloxy)-2H-isoquinolin-1-one | 7.4 | 24 |
| (S)-7-methyl-6-(piperidin-3-yloxy)-2H-isoquinolin-1-one | 7.3 | 28 |
| 6-(perhydroazepin-4-yloxy)-2H-isoquinolin-1-one | 6.8 | 24I |
| 6-[1-(1H-pyrrol-2-ylmethyl)-piperidin-3-yloxy]-isoquinolin-1-ylamine | 6.9 | 7F |
| (S)-6-[1-(4-methylbenzyl)piperidin-3-yloxy]isoquinolin-1-ylamine | 6.8 | 8D |
| 6-(piperidin-4-yloxy)-2H-isoquinolin-1-one | 6.7 | 24F |
| (R)-6-(1-benzylpiperidin-3-yloxy)isoquinolin-1-ylamine | 6.7 | 7AE |
| 6-[1-(2-phenoxyethyl)piperidin-3-yloxy]isoquinolin-1-ylamine | 6.7 | 21 |
| (3S)-6-[1-(1-phenylethyl)piperidin-3-yloxy]isoquinolin-1-ylamine | 6.7 | 21G |
| 6-(piperidin-4-ylsulfanyl)-2H-isoquinolin-1-one | 6.7 | 25 |
| 6-(1-thiophen-2-ylmethylpiperidin-3-yloxy)isoquinolin-1-ylamine | 6.6 | 7G |
| (S)-6-(1-benzylpiperidin-3-yloxy)isoquinolin-1-ylamine | 6.6 | 7 |
| (R)-6-[1-(2-phenoxyethyl)piperidin-3-yloxy]-2H-isoquinolin-1-one | 6.6 | 32E |
| (S)-6-[1-(4-fluorobenzyl)piperidin-3-yloxy]-isoquinolin-1-ylamine | 6.6 | 7I |
| (S)-4-bromo-6-(piperidin-3-yloxy)-2H-isoquinolin-1-one | 6.5 | 29 |
| 6-[1-(1H-pyrrol-2-ylmethyl)piperidin-4-yloxy]-2H-isoquinolin-1-one | 6.5 | 31G |
| 6-[1-(4-methoxybenzyl)piperidin-3-yloxy]-2H-isoquinolin-1-one | 6.4 | 23E |
| (S)-6-[1-furan-3-ylmethylpiperidin-3-yloxy]isoquinolin-1-ylamine | 6.4 | 7K |
| 6-[1-phenethylpiperidin-3-yloxy]isoquinolin-1-ylamine | 6.4 | 7J |
| 6-[1-(3-methoxybenzyl)piperidin-4-yloxy]-2H-isoquinolin-1-one | 6.4 | 31F |
| (S)-6-[1-(1H-pyrrol-3-ylmethyl)piperidin-3-yloxy]isoquinolin-1-ylamine | 6.3 | 7M |
| (S)-6-[1-(2-oxo-2-phenylethyl)piperidin-3-yloxy]-2H-isoquinolin-1-one | 6.3 | 32B |
| (S)-6-(pyrrolidin-3-yloxy)-2H-isoquinolin-1-one | 6.3 | 24H |
| 6-(1-cyclohexylmethylpiperidin-3-yloxy)-2H-isoquinolin-1-one | 6.3 | 33C |
| 6-(piperidin-3-ylsulfanyl)isoquinolin-1-ylamine | 6.3 | 12 |
| 6-(1-furan-2-ylmethylpiperidin-4-yloxy)-2H-isoquinolin-1-one | 6.3 | 30E |

TABLE I-continued

| Compound | ROCK-I pIC$_{50}$ | Example |
|---|---|---|
| (R)-6-(pyrrolidin-3-ylsulfanyl)isoquinolin-1-ylamine | 6.2 | 13B |
| (S)-4-methyl-6-(piperidin-3-yloxy)-2H-isoquinolin-1-one | 6.2 | 28 |
| (S)-6-(pyrrolidin-3-ylsulfanyl)isoquinolin-1-ylamine | 6.2 | 13A |
| 6-(1-methylpiperidin-4-yloxy)-2H-isoquinolin-1-one | 6.2 | 30G |
| (S) 6-(piperidin-3-yloxy)-isoquinolin-1-ylamine | 6.2 | 3 |
| 6-(piperidin-4-ylsulfanyl)isoquinolin-1-ylamine | 6.2 | 13C |
| (R)-6-(piperidin-3-yloxy)-2H-isoquinolin-1-one | 6.2 | 24E |
| (S)-6-[1-(2-phenoxyethyl)piperidin-3-yloxy]-2H-isoquinolin-1-one | 6.2 | 32C |
| 6-(1-benzylpiperidin-3-yloxy)-7-methylisoquinolin-1-ylamine | 6.1 | 19A |
| 6-[1-(3-hydroxypropyl)piperidin-4-yloxy]-2H-isoquinolin-1-one | 6.1 | 31C |
| 6-[1-(2-hydroxyethyl)piperidin-4-yloxy]-2H-isoquinolin-1-one | 6.1 | 3E |
| (R)-6-(pyrrolidin-3-yloxy)-2H-isoquinolin-1-one | 6.1 | 24G |
| 6-[1-(3-methylbenzyl)piperidin-4-yloxy]-2H-isoquinolin-1-one | 6.1 | 30A |
| 7-methyl-6-[1-(4-methylbenzyl)piperidin-3-yloxy]isoquinolin-1-ylamine | 6.0 | 19B |
| (S)-5-bromo-6-(piperidin-3-yloxy)-2H-isoquinolin-1-one | 6.0 | 27 |
| 6-[1-(4-methoxybenzyl)piperidin-4-yloxy]-2H-isoquinolin-1-one | 6.0 | 30C |

EXAMPLE 35

In-Vitro Determination of the Monocyte Migration Inhibitory Activity of Compounds of the Invention Human monocytic cells (THP-1) were suspended in migration medium (RPMI 1640 containing 0.1% BSA) at a concentration of 2×10$^6$ cells/ml in the presence and absence of inhibitory test compound. The cell suspension was then incubated for 30 min at 37° C. A solution of human Monocyte Chemotactic Protein 1 (MCP-1) at a concentration of 10 ng/ml in migration medium was then added to the lower chamber of the QCMTM Chemotaxis 59 µM 96-Well Cell Migration Kit (ECM512, Chemicon International). Following the introduction of the migration insert and a 10 min pre-equilibration step, 100 µl of the cell suspension was then added to the upper chamber and the kit incubated for 4 hrs at 37° C. under 5% carbon dioxide. Blank and Basal Migratory wells were also included, containing no cells and no MCP-1, respectively. The number of migratory cells was determined via the application of a lysis buffer and nucleic acid sensitive fluorescent dye (CyQuant GR dye, Molecular Probes). Fluorescence was then determined using the FlexStation Plate Reader. Percentage migration inhibition was calculated using the following equation:

Specific Migration Inhibition (%)=(1-{(Migrated cells in the presence of test compound-Basal Migrated Cells)/(Migrated cells in the absence of test compound-Basal Migrated Cells)} )×100.

The invention claimed is:

1. An isoquinoline having the Formula I

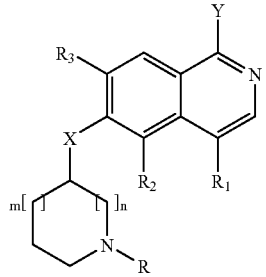

Formula I wherein
X is O, S or NH;
Y is OH or NH$_2$;
m is 0, 1 or 2;
n is 1 or 2;
R$_1$ is H, when Y is NH$_2$; or R$_1$ is H, (C$_{1-4}$)alkyl or halogen, when Y is OH;
R$_2$ and R$_3$ are independently H, (C$_{1-4}$)alkyl or halogen;
R is H or (C$_{1-6}$)alkyl, optionally substituted with OH, (C$_{1-4}$)alkyloxy, (C$_{1-4}$)-alkyloxycarbonyl, (C$_{3-7}$)cycloalkyl, which may optionally comprise a heteroatom selected from O and S, (C$_{6-10}$)aryl, (C$_{6-10}$)aryloxy or a 5- or 6-membered heteroaryl group comprising 1-3 heteroatoms independently selected from O, N and S, each aryl or heteroaryl group being optionally substituted with 1-3 substituents independently selected from (C$_{1-4}$)alkyl, (C$_{1-4}$)alkyloxy, (C$_{1-4}$)alkylsulfonyl and halogen; or a pharmaceutically acceptable salt thereof.

2. The isoquinoline of claim 1, wherein
X is O, S or NH;
Y is OH or NH$_2$;
R$_1$ and R$_2$ are H;
R$_3$ is H or (C$_{1-4}$)alkyl;
m is 0 or 1;
n is 1 or 2;
R is H or (C$_{1-4}$)alkyl, optionally substituted with (C$_{3-7}$) cycloalkyl, which may optionally comprise a heteroatom selected from O and S, (C$_{6-10}$)aryl or a 5- or 6-membered heteroaryl group comprising 1-3 heteroatoms independently selected from O, N and S, each aryl or heteroaryl group being optionally substituted with 1-3 substituents independently selected from (C$_{1-4}$)alkyl, (C$_{1-4}$)alkyloxy and halogen; or a pharmaceutically acceptable salt thereof.

3. The isoquinoline of claim 1, wherein Y is OH.

4. The isoquinoline of claim 1, wherein X is O.

5. The isoquinoline of claim 1, wherein R$_3$ is independently H, methyl or halogen, R$_1$ and R$_2$ are H, and R is H, (C$_{1-4}$)alkyl, optionally substituted with phenyl or a 5- or 6-membered (C$_{2-5}$)heteroaryl group comprising 1-3 heteroatoms selected from O, N and S, the phenyl or heteroaryl group being optionally substituted with 1-3 substituents selected from (C$_{1-4}$) alkyl, (C$_{1-4}$)alkyloxy and one or more halogens.

6. The isoquinoline of claim 1, wherein Y is OH, m is 1, n is 1 or 2, and R is H.

7. The isoquinoline which is selected from
(S)-6-(piperidin-3-yloxy)-2H-isoquinolin-1-one;
(S)-7-methyl-6-(piperidin-3-yloxy)-2H-isoquinolin-1-one;
6-(perhydroazepin-4-yloxy)-2H-isoquinolin-1-one;
(S)-6-[1-(1H-pyrrol-2-ylmethyl)-piperidin-3-yloxy]-isoquinolin-1-ylamine;
(S)-6-[1-(4-methylbenzyl)piperidin-3-yloxy]isoquinolin-1-ylamine;
6-(piperidin-4-yloxy)-2H-isoquinolin-1-one;
(R)-6-(1-benzylpiperidin-3-yloxy)isoquinolin-1-ylamine;
6-[1-(2-phenoxyethyl)piperidin-3-yloxy]isoquinolin-1-ylamine;
(3S)-6-[1-(1-phenylethyl)piperidin-3-yloxy]isoquinolin-1-ylamine;
6-(piperidin-4-ylsulfanyl)-2H-isoquinolin-1-one;
6-(1-thiophen-2-ylmethylpiperidin-3-yloxy)isoquinolin-1-ylamine;
(S)-6-(1-benzylpiperidin-3-yloxy)isoquinolin-1-ylamine;
(R) 6-[1-(2-phenoxyethyl)-piperidin-3-yloxy]-2H-isoquinolin-1-one;
(S)-6-[1-(4-fluorobenzyl)-piperidin-3-yloxy]-isoquinolin-1-ylamine;
(S)-4-bromo-6-(piperidin-3-yloxy)-2H-isoquinolin-1-one;
6-[1-(1H-pyrrol-2-ylmethyl)piperidin-4-yloxy]-2H-isoquinolin-1-one;
6-[1-(4-methoxybenzyl)piperidin-3-yloxy]-2H-isoquinolin-1-one;
(S)-6-[1-furan-3-ylmethylpiperidin-3-yloxy]isoquinolin-1-ylamine;
6-[1-phenethylpiperidin-3-yloxy]isoquinolin-1-ylamine;
6-[1-(3-methoxybenzyl)piperidin-4-yloxy]-2H-isoquinolin-1-one;
(S)-6-[1-(1H-pyrrol-3-ylmethyl)piperidin-3-yloxy]isoquinolin-1-ylamine;
(S)-6-[1-(2-oxo-2-phenylethyl)piperidin-3-yloxy]-2H-isoquinolin-1-one;
(S)-6-(pyrrolidin-3-yloxy)-2H-isoquinolin-1-one;
6-(1-cyclohexylmethylpiperidin-3-yloxy)-2H-isoquinolin-1-one;
6-(piperidin-3-ylsulfanyl)isoquinolin-1-ylamine;
6-(1-furan-2-ylmethylpiperidin-4-yloxy)-2H-isoquinolin-1-one.;
(R)-6-( pyrrolidin-3-ylsulfanyl)isoquinolin-1-ylamine;
(S)4-methyl-6-(piperidin-3-yloxy)-2H-isoquinolin-1-one;
(S)-6-( pyrrolidin-3-ylsulfanyl)isoquinolin-1-ylamine;
6-(1-methylpiperidin-4-yloxy)-2H-isoquinolin-1-one;
(S)-6-(piperidin-3-yloxy)-isoquinolin-1-ylamine;
6-(piperidin-4-ylsulfanyl)isoquinolin-1-ylamine;
(R)-6-(piperidin-3-yloxy)-2H-isoquinolin-1-one;
(S)-6-[1-(2-phenoxyethyl)piperidin-3-yloxy]-2H-isoquinolin-1-one;
6-(1-benzylpiperidin-3-yloxy)-7-methylisoquinolin-1-ylamine;
6-[1-(3-hydroxypropyl)piperidin-4-yloxy]-2H-isoquinolin-1-one;
6-[1-(2-hydroxyethyl)piperidin-4-yloxy]-2H-isoquinolin-1-one;
(R)-6-(pyrrolidin-3-yloxy)-2H-isoquinolin-1-one;
6-[1-(3-methylbenzyl)piperidin-4-yloxy]-2H-isoquinolin-1-one;
7-methyl-6-[1-(4-methylbenzyl)piperidin-3-yloxy]isoquinolin-1-ylamine;
(S)-5-bromo-6-(piperidin-3-yloxy)-2H-isoquinolin-1-one;
6-[1-(4-methoxybenzyl)piperidin-4-yloxy]-2H-isoquinolin-1-one, or a pharmaceutically acceptable salt thereof.

8. A pharmaceutical composition comprising an isoquinoline of claim 1, or a pharmaceutically acceptable salt thereof, in admixture with pharmaceutically acceptable auxilliaries.

9. A method for treating ROCK-I related disorders in a patient, the method comprising administering to the patient an effective amount of the isoquinoline according to claim 1.

10. The method of claim 9, wherein the ROCK-I related disorders are selected from the group consisting of hypertension, atherosclerosis and glaucoma.

* * * * *